(12) United States Patent
Di Martino et al.

(10) Patent No.: US 7,691,411 B2
(45) Date of Patent: *Apr. 6, 2010

(54) PHARMACEUTICAL FORMULAE FOR THYROID HORMONES AND PROCEDURES FOR OBTAINING THEM

(75) Inventors: Alessandro Di Martino, Casalzuigno (IT); Angel Mateo, Segrate (IT); Alberto Garavani, Ponte Capriasca (CH); Maurizio Marchiorri, Valbrona (IT)

(73) Assignee: Altergon S.A., Lugano (CH)

( * ) Notice: Subject to any disclaimer, the term of this patent is extended or adjusted under 35 U.S.C. 154(b) by 1093 days.

This patent is subject to a terminal disclaimer.

(21) Appl. No.: 10/746,386

(22) Filed: Dec. 23, 2003

(65) Prior Publication Data

US 2004/0219218 A1    Nov. 4, 2004

(30) Foreign Application Priority Data

Dec. 27, 2002    (IT)    ............... MI2002A2777

(51) Int. Cl.
*A61K 9/14* (2006.01)
*A61K 9/48* (2006.01)
*A61K 9/66* (2006.01)
*A61K 9/64* (2006.01)

(52) U.S. Cl. ............... 424/488; 424/451; 424/455; 424/456; 424/484; 424/486

(58) Field of Classification Search ............... 424/400, 424/451, 464, 484, 488
See application file for complete search history.

(56) References Cited

U.S. PATENT DOCUMENTS

| 6,395,299 B1 * | 5/2002 | Babich et al. |
| 6,790,453 B2 * | 9/2004 | Porzio et al. |
| 6,852,688 B2 * | 2/2005 | Grant |

FOREIGN PATENT DOCUMENTS

| GB | 1180574 | 2/1970 |
| WO | 02/89917 | * 11/2002 |
| WO | WO02089917 | 11/2002 |
| WO | 1291021 | 3/2003 |

* cited by examiner

*Primary Examiner*—Humera N Sheikh
(74) *Attorney, Agent, or Firm*—Abelmane, Frayne & Schwab

(57) ABSTRACT

The present invention provides pharmaceutical formulation for thyroid hormones which allow safe and stable administration by mouth within the ambit of the narrow therapeutic index prescribed in the case of thyroid dysfunctions, as well as procedures for obtaining them.

32 Claims, No Drawings

PHARMACEUTICAL FORMULAE FOR THYROID HORMONES AND PROCEDURES FOR OBTAINING THEM

FIELD OF THE INVENTION

The present invention concerns pharmaceutical formulation for thyroid hormones and procedures for obtaining them.

PRIOR ART

T3 and T4 are thyroid hormones and are used for various therapeutic applications. T3 (liothyronine=O-(4-hydroxy-3-iodophenyl)-3,5-diiodo-L-thyroxine) and T4 (levothyroxine or levothyroxina=O-(4-hydroxy-3,5-diiodophenyl)-3,5-diiodo-L-thyroxine), as such or in the form of sodium or hydrate salts are widely known and obtained by synthesis and/or extraction from animal glands (e.g.: pig etc.).

In particular, these thyroid hormones have two important functions: they intervene in the development, especially in the central nervous system and they act in the adult maintaining the metabolic homeostasis and virtually influencing the function of all the organs. The concentrations in the serum of the thyroid hormones are precisely regulated by the hormone tyrotropin with a classic negative feedback system. However, the treatment of the lack of these hormones gives satisfactory results with the administration of T3 and T4 (or of their respective sodium salts) and most patients can be treated by taking them.

In particular, T3 and T4 are used above all in the treatment of hypothyroidism. Hypothyroidism is a very common complaint. In the United States, 1 newborn out of 4000-5000 has hypothyroidism, while hyperthyroidism appears later in 0.5-1.3 percent of adults. In the population over sixty, the incidence of hypothyroidism increases, reaching 2.7 percent in men and 7.1 percent in women. Since congenital hypothyroidism can result in irreversible mental retardation, which can however be prevented by diagnosis and treatment in its initial stages, screening of this condition in the newborn is obligatory in North America, Europe and Japan.

As well as for treating hypothyroidism, for example, T4 (sodium salt of levothyroxine) can be used to suppress the secretion of tyrotropin in the treatment of simple non-endemic goitre, of chronic lymphocytic thyroiditis and of cancer of the thyroid. Sodium salt of levothyroxine is also used together with antithyroid agents in the treatment of thyrotoxicosis to prevent the onset of goitre and hypothyroidism.

Often, the therapy of supplementing with thyroid hormones continues throughout the patient's life. Moreover, the dosing must be individually established for each patient. Generally, the initial dose is small. The quantity is then gradually increased until clinical assessment and laboratory tests indicate that an optimum response is being received in the treated organism. The dose needed to obtain this response is then maintained. The age and general physical condition of the patient and the severity and duration of the symptoms of hypothyroidism determine the initial dose and the speed at which the dose can be brought to its definitive level. It is particularly important to increase the doses only very gradually in patients with myxedema or with cardiovascular diseases to prevent the onset of angina, myocardial infarction or ictus.

For these reasons T3 and T4, their respective sodium salts and their combination (Liotrix), have always been administered by mouth, in particular in the is form of tablets which, by checking the frequency with which they are taken and choosing the dosing units, allow the supplement to be adapted to the individual situation of the patient.

In fact, precise dosing is extremely critical since under-dosing would lead to a less than optimum response and therefore to hypothyroidism. On the other hand, excessive dosing would lead to toxic manifestations of hyperthyroidism such as, for example, cardiac pain, palpitations, or cardiac arrhythmia. In patients suffering from coronary diseases, even a minimum increase of the dose of levothyroxine can be dangerous.

Hyperthyroidism is also a well-known risk factor for osteoporosis. To minimise the risk of osteoporosis, it is therefore recommended to calculate the dose as precisely as possible until the minimum effective dose is obtained.

So, on account of the risks associated with over-dosing or under-dosing, not only of sodium salt of levothyroxine, but of thyroid hormones in general, it is absolutely critical that the patients can rely on pharmaceutical products that are reliable in terms of titre and bio-availability. The reaching and above all the maintaining of these particularly strict criteria therefore present considerable difficult.

For example, between 1987 and 1994 the United States Food and Drug Administration ("FDA") received 58 reports of irregular experiences associated with the power (titre) of sodium levothyroxine products administered by mouth. 47 of these reports suggested that the titre of the pharmaceutical preparations was lower than the declared value, while 9 suggested that the titre was higher. Two of the reports concerned inconsistencies in the blood level of thyroid hormones. Four of the reports resulted in hospitalisation, 2 of them being attributed to under-dosage and the other 2 to over-dosage. More than half of the total of 58 reports were backed up by blood tests of thyroid function. Among the specific symptoms of hypothyroidism, the following were recorded: severe depression, fatigue, weight increase, constipation, intolerance to cold, oedema, and difficulty in concentration. The specific symptoms of hyperthyroidism included atrial fibrillation, palpitation of the heart and insomnia.

While some problems appeared at the time of changing the brand of the pharmaceutical product, many of the problems also appeared when the patients only took further quantities of a product that had already been administered to them for a long time and which had previously allowed satisfactory treatment, indicating poor consistency in terms of stability, titre and bio-availability between different batches from the same manufacturer.

While it is clear that thyroid hormones, in particular T3, T4 and a combination of the two, represent necessary medications in many cases where there are no acceptable substitutes, there is however the problem that—in view of the very strict therapeutic index to which the dosing of thyroid hormones is subjected—it is particularly important that the quantity of active principle available be absolutely reliable for a given unit of pharmaceutical dosage.

On account of the difficulties encountered with traditional formulae, it has been known for some time that it is necessary to obtain pharmaceutical formulae for the administration of thyroid hormones, particularly of T3 or T4 and the combination of the two, preferably by mouth, which are more reliable in terms of titre and bio-availability. In particular, for some time it has been necessary to obtain pharmaceutical formulae for the preferably oral administration of thyroid hormones, in particular T3 or T4 and the combination of the two, which remains stable in time, that is which has an effective shelf-life of at least two years. Moreover, it is necessary to obtain pharmaceutical formulae for the administration of thyroid hormones, particularly of T3 or T4 and the combination of the two, which make it possible to obtain perfectly uniform dosing, not only irrespective of the production batch, but preferably also within the same pharmaceutical dosing unit.

The present invention therefore aims to satisfy these and other necessities will be clearer from the following detailed description.

SUMMARY

According to a first aspect of the present invention, it was found that the disadvantages of the prior art can be overcome by providing pharmaceutical compositions of thyroid hormones in a uniform matrix of soft-gel which can be taken by mouth without chewing, in which the uniform matrix has the form and dimensions of a tablet or capsule, said pharmaceutical compositions comprising, in the dried state, 30%-68% in weight of gelatine of bovine, pig or fish origin, thyroid hormones, preferably T3 and/or T4 or their salts, in a pharmaceutically effective combination, and characterised in that they comprise, in the dried state, 31-60% in weight, preferably 32-55% in.weight of glycerol and 1-10% in weight of water.

According to a second aspect of the present invention, it was found that the disadvantages of the prior art can be overcome by providing pharmaceutical compositions of thyroid hormones in a uniform matrix of soft-gel which can be taken by mouth without chewing, in which the uniform matrix has the form and dimensions of a tablet or capsule, said pharmaceutical compositions comprising, in the dried state, 30%-70% in weight of gelatine of bovine, pig or fish origin, thyroid hormones, preferably T3 and/or T4 or their salts, in a pharmaceutically effective combination, and characterised in that they comprise, in the dried state, 20-60% in weight, preferably 25-55% in weight of sorbitol/sorbitans and 1-10% in weight of water.

DETAILED DESCRIPTION OF THE INVENTION

In particular, according to a first aspect of the present invention, it was found that the pharmaceutical formula of thyroid hormones (in particular of T3 and/or T4 or their salts, preferably their sodium salts) in a uniform matrix of soft-gel which can be taken by mouth without chewing (and that is in which the uniform matrix is composed of a three-dimensional body having the form and dimensions of a normal tablet or intense capsule for taking orally), said matrix comprising, in the dried state, 30%-68% in weight of gelatine of bovine, pig or fish origin, and characterised in that they comprise, in the dried state, 31-60% in weight, preferably 32-55% in weight of glycerol and 1-10% in weight of water, offers considerable advantages in relation to normal administration in the known pharmaceutical forms which did not have an acceptable shelf-life.

By the term dried state is meant, preferably, the state reached by the pharmaceutical formula after drying at a temperatures of 20° C.-24° C. and a relative humidity of 20% with a continuous change of the surrounding air until a constant weight is reached, that is until two weighing operations carried out at a distance of 24 hours do not vary by more than 1%.

The uniform matrices of soft-gel of the present invention comprise T3 and/or T4 or their salts, preferably their sodium salts, in pharmaceutically acceptable quantities, preferably 0.001-1% in weight.

Optionally, the uniform matrices of soft-gel of the present invention may be provided on the outside with enteric layers formulated according to known techniques so that they decompose substantially in the environment of the small intestine which is the principal site of absorption of thyroid hormones.

Besides (or instead of) enteric layers, the uniform matrices of soft-gel of the present invention may optionally present also further layers that facilitate ingestion, that is which are composed of excipients that reduce friction between the capsule and the patient's oesophagus.

The materials used to obtain the uniform matrices of soft-gel of the present invention are the so-called type A or B gelatines of bovine, pig and fish origin usually used in pharmaceutical technique for making capsules. In the uniform matrices of soft-gel of the present invention, the gelatines are present, in the dried product, from 30% to 68% in weight. A representative, but not exclusive example of a gelatine that may be used in the present invention is a gelatine with the following amino acidic profile: Glycine: 26%, Alanine: 9%, Isoleucine: 1.5%, Leucine: 3.4%, Valine: 2.5%, Serine: 3.5%, Threonine: 2%, Proline: 16%, Phenylalanine: 2.4%, Tyrosine: 0.8%, Tryptophane: 0%, Methionine: 0.8%, Histidine: 0.8%, Arginine: 9%, Lysine: 5%, Aspartic acid: 6%, Glutamic acid: 11%, Hydroxyproline: 13.5% and Hydroxylysine: 1%. Preferably, the gelatines that may be used in the present invention have a grain size between 4 and 100 mesh and a pH between 3 and 10.

The solvent used necessarily in obtaining the uniform matrices of soft-gel of the present invention is glycerol, which must be present, in the dried product, with 31-60% in weight, preferably with 32-55% in weight, even more preferably with 32.5%-50% in weight.

A further solvent used in obtaining the uniform matrices of soft-gel of the present invention is water, which remains present, in the dried product, in a quantity of 1-10% in weight.

A further solvent that may be used in obtaining the uniform matrices of soft-gel of the present invention is ethanol which, when used, remains present, in the dried product, in a quantity of 0.5-5% in weight.

Further solvents which may be used in obtaining the uniform matrices of soft-gel of the present invention are other polyhydroxy or polyether alcohols, such as for example sorbitol/sorbitans, 1,2-propylenglycol, polyethylenglycols and mannitol or mixtures thereof. When these further solvents are used, they or their mixtures are added in quantities such as to remain present, altogether, in the dried product, in a quantity of 3-10% in weight.

Further components that may be used in obtaining the uniform matrices of soft-gel of the present invention are excipients, for example all the usual pharmaceutically acceptable solid additives which may be used to modify the characteristics of the release of thyroid hormones from the resulting uniform matrix of soft-gel. Further excipients that may be used in obtaining the uniform matrices of soft-gel of the present invention are colouring agents and/or preservatives such as parabenes, preferably methylparahydroxybenzoate, ethylparaoxybenzoate or propylparahydroxybenzoate.

According to a particularly advantageous aspect of the present invention, the pharmaceutical formulae of thyroid hormones in uniform matrices of soft-gel can be obtained with two different procedures which both use the so-called "Rotary Die" machines commonly used in the pharmaceutical technique for producing soft capsules with a liquid or semi-liquid content.

The specific contrivances proposed by the procedures of the present invention mean that, instead of the classic two-phase capsules, comprising a casing and a content of different consistency, "full" capsules are obtained, that is uniform matrices of soft-gel which are perfectly single-phase.

According to a first procedure concerning the first aspect of the present invention, all the necessary components for obtaining the pharmaceutical composition in a uniform matrix of soft-gel of the present invention are mixed and the mixture is fed into a "Rotary Die" type machine for forming capsules, which then forms "full" capsules without injected material. These "full" capsules constitute the pharmaceutical compositions in uniform matrices of soft-gel of the present invention.

According to a first variation of the first procedure concerning the first aspect of the present invention, all the necessary components for obtaining the pharmaceutical composition in a uniform matrix of soft-gel of the present invention are mixed, obtaining a medicated gelatinous mixture, the medicated gelatinous mixture is brought to melting point and fed into a "Rotary Die" type machine for forming capsules, which then forms "full" capsules without injected material. These "full" capsules constitute the pharmaceutical compositions in uniform matrices of soft-gel of the present invention.

In particular, according to the first variation of the first procedure concerning the first aspect of the present invention, to prepare a pharmaceutical composition of thyroid hormones in a uniform matrix of soft-gel, the following steps are performed:

preparation of a medicated gelatinous mixture comprising 10-50% in weight of type A or B gelatine of bovine, pig or fish origin, 10-50% in weight of glycerol, 0-10% in weight of ethanol, 20-80% in weight of water and 0.001-1% in weight of T3 and/or T4 or their salts, melting of the medicated gelatinous mixture at a temperature between 30° and 55° C., preferably between 35° and 45° C., feeding of the medicated gelatinous mixture into the cavities of the shaping cylinders of a "Rotary Die" type machine for forming capsules, cutting and taking the pharmaceutical composition in a uniform matrix of soft-gel thus formed from the "Rotary Die" machine, and drying of the pharmaceutical composition in a uniform matrix of soft-gel.

Preferably, the "Rotary Die" machines are operated in an environment having a temperature between 20° C. and 24° C. and a relative humidity between 5% and 35%, preferably around 20%. Preferably, the pharmaceutical composition in a uniform matrix of soft-gel obtained as above is dried at a temperature of 20° C.-24° C. and a relative humidity of 20% with a continuous change of the surrounding air until a constant weight is obtained, that is until two weighing operations carried out at an interval of 24 h do not differ by more than 1%.

If contemplated, further solvents, such as polyhydroxy or polyether alcohols, excipients, preservatives and/or colouring agents can be added to the medicated gelatinous mixture obtained in the first step.

According to a second variation of the first procedure concerning the first aspect of as the present invention, some of the necessary components for obtaining the pharmaceutical composition in a uniform matrix of soft-gel of the present invention are mixed, among which gelatine, obtaining a gelatinous mixture, the gelatinous mixture is brought to melting point, a medicated composition containing the active principle is added to it, obtaining a medicated gelatinous mixture and it is fed into a "Rotary Die" type machine for forming capsules, which then forms "full" capsules without injected material. These "full" capsules constitute the pharmaceutical compositions in uniform matrices of soft-gel of the present invention.

In particular, according to the second variation of the first procedure concerning the first aspect of the present invention, to prepare a pharmaceutical composition of thyroid hormones in a uniform matrix of soft-gel, the following steps are performed:

preparation of a gelatinous mixture comprising 10-50% in weight of type A or B gelatine of bovine, pig or fish origin, 5-45% of glycerol, 0-10% in weight of ethanol and 20-60% in weight of water, melting of the gelatinous mixture at a temperature between 30° and 80° C., preferably between 40° and 65° C., when it is completely melted, lowering of the temperature of the gelatinous mixture to 45°±5° C. and addition of a medicated mixture comprising T3 and/or T4 or their salts as required and glycerol, the quantity of the medicated mixture corresponding to 5%-10% in weight of the gelatinous mixture, obtaining a medicated gelatinous mixture, feeding of the medicated gelatinous mixture into the cavities of the shaping cylinders of a "Rotary Die" type machine for forming capsules, cutting and taking the pharmaceutical composition in a uniform matrix of soft-gel thus formed from the "Rotary Die" machine, and drying of the pharmaceutical composition in a uniform matrix of soft-gel.

If contemplated, further solvents, such as polyhydric or polyether alcohols, excipients, preservatives and/or colouring agents can be added to the gelatinous mixture obtained in the first step and/or to the medicated mixture added in the third step.

Preferably, the "Rotary Die" machines are operated in an environment having a temperature between 20° C. and 24° C. and a relative humidity between 5% and 35%, preferably around 20%. Preferably, the pharmaceutical composition in a uniform matrix of soft-gel obtained as above is dried at a temperature of 20° C.-24° C. and a relative humidity of 20% with a continuous change of the surrounding air until a constant weight is obtained, that is until two weighing operations carried out at an interval of 24 h do not differ by more than 1%.

A second procedure (which is particularly preferred) for obtaining pharmaceutical formulae of thyroid hormones in uniform matrices of soft-gel according to the first aspect of the present invention, contemplates the dissolving/suspension of the active principle and of any excipients in a liquid vehicle to give the so-called "medicated injected material" which is then injected into the gelatinous mixture at the time of forming the matrix. The components of the gelatinous mixture and respectively, of the medicated injected material, are particularly calibrated to allow the uniform diffusion of the medicated injected material in the matrix, without altering its single-phase structure. Consequently, also with the second procedure concerning the first aspect of the present invention, the usual soft capsules filled with a liquid, semi-liquid or pasty phase are not obtained, but rather a matrix of uniform soft-gel comprising the active principle.

In particular, to prepare a pharmaceutical composition of thyroid hormones in a uniform matrix of soft-gel according to the second procedure concerning the first aspect of the present invention, the following steps are performed:

preparation of a gelatinous mixture comprising 10-50% in weight of type A or B gelatine of bovine, pig or fish origin, 10-50% in weight of glycerol, 0-10% in weight of ethanol, 20-80% in weight of water, melting of the gelatinous mixture at a temperature between 30-80° C. preferably between 40-65° C., feeding of the gelatinous mixture into the cavities of the shaping cylinders of a "Rotary Die" type machine for forming capsules; injection, at the time of closing the cavity, by means of the special injector, of a quantity of medicated injected material corresponding to from 1% to 50% in weight, preferably to from 5% to 30% in weight, of the quantity of gelatinous mixture placed in the cavity, said medicated injected material comprising
30-95% in weight of glycerol,
0-50% in weight of ethanol,
0-50% in weight of water,
0-50% in weight of gelatine as much as necessary in weight of T3 and/or T4, cutting and taking the pharmaceutical composition in a uniform matrix of soft-gel thus formed from the "Rotary Die" machine, and drying of the pharmaceutical composition in a uniform matrix of soft-gel.

Preferably, the medicated injected material comprises 50%-90% in weight of glycerol, 0%-30% in weight of ethanol, 0%-45% in weight of water, 5%-20% in weight of gelatine, and as much as necessary in weight of T3 and/or T4.

Even more preferably, the medicated injected material comprises 60%-90% in weight of glycerol, 5%-15% in weight of water, 5-10% of gelatine and as much as necessary in weight of T3 and/or T4.

Even more preferably, the medicated injected material comprises 50-70% in weight of glycerol, 25%-30% in weight of ethanol, 5%-10% of gelatine and as much as necessary in weight of T3 and/or T4.

Even more preferably, the medicated injected material comprises 50-70% in weight of glycerol, 25%-45% in weight of water, 5%-10% of gelatine and as much as necessary in weight of T3 and/or T4.

If contemplated, further solvents, such as polyhydroxy or polyether alcohols, excipients, preservatives and/or colouring agents can be added to the gelatinous mixture obtained in the first step and/or to the medicated injected material added in the third step.

Preferably, the "Rotary Die" machines are operated in an environment having a temperature between 20° C. and 24° C. and a relative humidity between 5% and 35%, preferably around 20%. Preferably, the pharmaceutical composition in a uniform matrix of soft-gel obtained as above is dried at a temperature of 20° C.-24° C. and a relative humidity of 20% with a continuous change of the surrounding air until a constant weight is obtained, that is until two weighing operations carried out at an interval of 24 h do not differ by more than 1%.

As has already been said, in the working conditions indicated above, the medicated injected material never remains a liquid or pasty phase, distinguishable from the gelatinous phase, but is spread uniformly in the gelatinous mixture, to give a uniform matrix of soft-gel which can be taken by mouth.

Moreover, according to a second aspect of the present invention it was found that the pharmaceutical formula of thyroid hormones (in particular of T3 and/or T4 or their salts, preferably their sodium salts) in a uniform matrix of soft-gel which can be taken by mouth without chewing (and that is in which the uniform matrix is composed of a three-dimensional body having the form and the dimensions of a normal tablet or intense capsule for taking orally), said matrix comprising, in the dried state, 30%-70% in weight of gelatine of bovine, pig or fish origin, and characterised in that they comprise, in the dried state, 20-60% in weight, preferably 25-55% in weight of sorbitol/sorbitans and 1-10% in weight of water, offers considerable advantages in relation to normal administration in the known pharmaceutical forms which did not have an acceptable shelf-life.

By the term dried state is meant, preferably, the state reached by the pharmaceutical formula after drying at a temperatures of 20° C.-24° C. and a relative humidity of 20% with a continuous change of the surrounding air until a constant weight is reached, that is until two weighing operations carried out at a distance of 24 hours do not vary by more than 1%.

The uniform matrices of soft-gel of the present invention comprise T3 and/or T4 or their salts, preferably their sodium salts, in pharmaceutically acceptable quantities, preferably 0.001-1% in weight. Optionally, the uniform matrices of soft-gel of the present invention may be provided on the outside with enteric layers formulated according to known techniques so that they decompose substantially in the environment of the small intestine which is the principal site of absorption of thyroid hormones.

Besides (or instead of) enteric layers, the uniform matrices of soft-gel of the present invention may be optionally provided with also further layers that facilitate ingestion, that is which are composed of excipients that reduce friction between the capsule and the patient's oesophagus.

The materials used to obtain the uniform matrices of soft-gel of the present invention are the so-called type A or B gelatines of bovine, pig and fish origin usually used in pharmaceutical technique for making capsules. In the uniform matrices of soft-gel of the present invention, the gelatines are present, in the dried product, from 30% to 70% in weight. A representative, but not exclusive example of a gelatine that may be used in the present invention is a gelatine with the following amino acidic profile: Glycine: 26%, Alanine: 9%, Isoleucine: 1.5%, Leucine: 3.4%, Valine: 2.5%, Serine: 3.5%, Threonine: 2%, Proline: 16%, Phenylalanine: 2.4%, Tyrosine: 0.8%, Tryptophane: 0%, Methionine: 0.8%, Histidine: 0.8%, Arginine: 9%, Lysine: 5%, Aspartic acid: 6%, Glutamic acid: 11%, Hydroxyproline: 13.5% and Hydroxylysine: 1%. Preferably, the gelatines that may be used in the present invention have a grain size between 4 and 100 mesh and a pH between 3 and 10.

The solvent used necessarily in obtaining the uniform matrices of soft-gel of the present invention is a mixture of sorbitol/sorbitans, which must be present, in the dried product, with 20-60% in weight, preferably with 25-55% in weight, even more preferably with 25-50% in weight.

A further solvent-used in obtaining the uniform matrices of soft-gel of the present invention is water, which remains present, in the dried product, in a quantity of 1-10% in weight.

A further solvent that may be used in obtaining the uniform matrices of soft-gel of the present invention is ethanol which, when used, remains present, in the dried product, in a quantity of 0.5-5% in weight.

Further solvents which may be used in obtaining the uniform matrices of soft-gel of the present invention are other polyhydroxy or polyether alcohols, such as for example glycerol, 1,2-propylenglycol, polyethylenglycols and mannitol or mixtures thereof. When these further solvents are used, they or their mixtures are added in quantities such as to remain present, altogether, in the dried product, in a quantity of 1-10% in weight. Among the further solvents as above, glycerol is particularly preferred.

Further components that may be optionally used for obtaining the uniform matrices of soft-gel of the present invention are excipients, for example all the usual pharmaceutically acceptable solid additives which may be used to modify the characteristics of the release of thyroid hormones from the resulting uniform matrix of soft-gel. Further excipients that may be used in obtaining the uniform matrices of soft-gel of the present invention are colouring agents and/or preservatives such as parabenes, preferably methylparahydroxybenzoate, ethylparaoxybenzoate or propylparahydroxybenzoate.

According to a particularly advantageous aspect of the present invention, the pharmaceutical formulations of thyroid hormones in uniform matrices of soft-gel can be obtained with two different procedures which both use the so-called "Rotary Die" machines commonly used in the pharmaceutical technique for producing soft capsules with a liquid or semi-liquid content.

The specific contrivances proposed by the procedures of the present invention mean that, instead of the classic two-phase capsules, comprising a casing and a content of different consistency, "full" capsules are obtained, that is uniform matrices of soft-gel which are perfectly single-phase.

According to a first procedure concerning the second aspect of the present invention, all the necessary components for obtaining the pharmaceutical composition in a uniform matrix of soft-gel of the present invention are mixed and the mixture is fed into a "Rotary Die" type machine for forming capsules, which then forms "full" capsules without injected material. These "full" capsules constitute the pharmaceutical compositions in uniform matrices of soft-gel of the present invention.

According to a first variation of the first procedure concerning the second aspect of the present invention, all the necessary components for obtaining the pharmaceutical composition in a uniform matrix of soft-gel of the present invention are mixed, obtaining a medicated gelatinous mixture, the medicated gelatinous mixture is brought to melting point and fed into a "Rotary Die" type machine for forming capsules, which then forms "full" capsules without injected material. These "full" capsules constitute the pharmaceutical compositions in uniform matrices of soft-gel of the present invention.

In particular, according to the first variation of the first procedure concerning the second aspect of the present invention, to prepare a pharmaceutical composition of thyroid hormones in a uniform matrix of soft-gel, the following steps are performed:

preparation of a medicated gelatinous mixture comprising 10-50% in weight of type A or B gelatine of bovine, pig or fish origin, 10-50% in weight of sorbitol/sorbitans solution, 0-10% in weight of ethanol, 20-80% in weight of water and 0.001-1% in weight of T3 and/or T4 or their salts, melting of the medicated gelatinous mixture at a temperature between 30° and 55° C., preferably between 35° and 45° C., feeding of the medicated gelatinous mixture into the cavities of the shaping cylinders of a "Rotary Die" type machine for forming capsules, cutting and taking the pharmaceutical composition in a uniform matrix of soft-gel thus formed from the "Rotary Die" machine, and drying of the pharmaceutical composition in a uniform matrix of soft-gel.

Solutions of sorbitol/sorbitans are available on the market, for example Anidrisorb 85 which contains a mixture of sorbitol/sorbitans and 15% of water.

Preferably, the "Rotary Die" machines are operated in an environment having a temperature between 20° C. and 24° C. and a relative humidity between 5% and 35%, preferably around 20%. Preferably, the pharmaceutical composition in a uniform matrix of soft-gel obtained as above is dried at a temperature of 20° C.-24° C. and a relative humidity of 20% with a continuous change of the surrounding air until a constant weight is obtained, that is until two weighing operations carried out at an interval of 24 h do not differ by more than 1%.

If contemplated, further solvents, such as polyhydroxy or polyether alcohols, in particular glycerol, excipients, preservatives and/or colouring agents can be added to the medicated gelatinous mixture obtained in the first step.

According to a second variation of the first procedure concerning the second aspect of the present invention, some of the necessary components for obtaining the pharmaceutical composition in a uniform matrix of soft-gel of the present invention are mixed, among which gelatine, obtaining a gelatinous mixture, the gelatinous mixture is brought to melting point, a medicated composition containing the active principle is added to it, obtaining a medicated gelatinous mixture and it is fed into a "Rotary Die" type machine for forming capsules, which then forms "full" capsules without injected material. These "full" capsules constitute the pharmaceutical compositions in uniform matrices of soft-gel of the present invention.

In particular, according to the second variation of the first procedure concerning the second aspect of the present invention, to prepare a pharmaceutical composition of thyroid hormones in a uniform matrix of soft-gel, the following steps are performed:

preparation of a gelatinous mixture comprising 10-50% in weight of type A or B gelatine of bovine, pig or fish origin, 10-50% of sorbitol/sorbitan solution, 0-10% in weight of ethanol and 20-60% in weight of water, melting of the gelatinous mixture at a temperature between 30° and 80° C., preferably between 40° and 65° C., when it is completely melted, lowering of the temperature of the gelatinous mixture to 45±5° C. and addition of a medicated mixture comprising T3 and/or T4 or their salts as required and glycerol, the quantity of the medicated mixture corresponding to 1%-5% in weight of the gelatinous mixture, obtaining a medicated gelatinous mixture, feeding of the medicated gelatinous mixture into the cavities of the shaping cylinders of a "Rotary Die" type machine for forming capsules, cutting and taking the pharmaceutical composition in a uniform matrix of soft-gel thus formed from the "Rotary Die" machine, and drying of the pharmaceutical composition in a uniform matrix of soft-gel.

Solutions of sorbitol/sorbitans are available on the market, for example Anidrisorb 85 which contains a mixture of sorbitol/sorbitans and 15% of water.

If contemplated, further solvents, such as polyhydroxy or polyether alcohols, excipients, preservatives and/or colouring agents can be added to the gelatinous mixture obtained in the first step and/or to the medicated mixture added in the third step.

Preferably, the "Rotary Die" machines are operated in an environment having a temperature between 20° C. and 24° C. and a relative humidity between 5% and 35%, preferably around 20%. Preferably, the pharmaceutical composition in a uniform matrix of soft-gel obtained as above is dried at a temperature of 20° C.-24° C. and a relative humidity of 20% with a continuous change of the surrounding air until a constant weight is obtained, that is until two weighing operations carried out at an interval of 24 h do not differ by more than 1%.

A second procedure (which is particularly preferred) for obtaining pharmaceutical formulae of thyroid hormones in uniform matrices of soft-gel according to the second aspect of the present invention, contemplates the dissolving/suspension of the active principle and of any excipients in a liquid vehicle to give the so-called "medicated injected material" which is then injected into the gelatinous mixture at the time of forming the matrix. The components of the gelatinous mixture and respectively, of the medicated injected material, are particularly calibrated to allow the uniform diffusion of the medicated injected material in the matrix, without altering its single-phase structure. Consequently, also with the second procedure concerning the second aspect of the present invention, the usual soft capsules filled with a liquid, semi-liquid or pasty phase are not obtained, but rather a matrix of uniform soft-gel comprising the active principle.

In particular, to prepare a pharmaceutical composition of thyroid hormones in a uniform matrix of soft-gel according to the second procedure concerning the second aspect of the present invention, the following steps are performed:

preparation of a gelatinous mixture comprising 10-50% in weight of type A or B gelatine of bovine, pig or fish origin, 10-50% in weight of sorbitol/sorbitans solution, 0-10% in weight of ethanol, 20-80% in weight of water, melting of the gelatinous mixture at a temperature between 30-80° C. preferably between 40-65° C, feeding of the geltinous mixture into the cavities of the shaping cylinders of a "Rotary Die" type machine for forming capsules; injection, at the time of closing the cavity, by means of the special injector, of a quantity of medicated injected material corresponding to from 1% to 30% in weight, preferably to from 5% to 15% in weight, of the quantity of gelatinous mixture placed in the cavity, said medicated injected material comprising 25-95% in weight of glycerol,
0-50% in weight of ethanol,
0-50% in weight of water,
0-50% in weight of gelatine, as much as necessary in weight of T3 and/or T4, cutting and taking the pharmaceutical composition in a uniform matrix of soft-gel thus formed from the "Rotary Die" machine, and drying of the pharmaceutical composition in a uniform matrix of soft-gel.

Solutions of sorbitol/sorbitans are available on the market, for example Anidrisorb 85 which contains a mixture of sorbitol/sorbitans and 15% of water. Preferably, the medicated injected material comprises 50%-90% in weight of glycerol, 0%-30% in weight of ethanol, 5%-45% in weight of water, 0%-20% in weight of gelatine, and as much as necessary in weight of T3 and/or T4.

Even more preferably, the medicated injected material comprises 60%-90% in weight of glycerol, 5%-15% in weight of water, 0-50% weight of gelatine, and as much as necessary in weight of T3 and/or T4.

Even more preferably, the medicated injected material comprises 50-70% in weight of glycerol, 25%-30% in weight of ethanol, 5%-10% of gelatine and as much as necessary in weight of T3 and/or T4.

Even more preferably, the medicated injected material comprises 50-70% in weight of glycerol, 25%-45% in weight of water, 0%-10% of gelatine and as much as necessary in weight of T3 and/or T4.

If contemplated, further solvents, such as polyhydric or polyether alcohols, excipients, preservatives and/or colouring agents can be added to the gelatinous mixture obtained in the first step and/or to the medicated injected material added in the third step.

Preferably, the "Rotary Die" machines are operated in an environment having a temperature between 20° C. and 24° C. and a relative humidity between 5% and 35%, preferably around 20%. Preferably, the pharmaceutical composition in a uniform matrix of soft-gel obtained as above is dried at a temperature of 20° C.-24° C. and a relative humidity of 20% with a continuous change of the surrounding air until a constant weight is obtained, that is until two weighing operations carried out at an interval of 24 h do not differ by more than 1%.

As has already been said, in the working conditions indicated above, the medicated injected material never remains a liquid or pasty phase, distinguishable from the gelatinous phase, but is spread uniformly in the gelatinous mixture, to give a uniform matrix of soft-gel which can be taken by mouth.

Consequently, the pharmaceutical compositions of thyroid hormones in a uniform matrix of soft-gel according to both aspects of the present invention can be easily divided by the patient—unlike the normal soft capsules with a liquid or semi-liquid content—to make an adaptation of the individual dose prescribed by the doctor.

EXPERIMENTAL PART

Below are given some examples of formulae according to the present invention:

Example 1

The following formulae concern the first aspect of the present invention and were obtained according to the second procedure of the present invention:

The first three columns refer to the initial situation, that is before injection:

First column: percentage composition of the medicated injected material and of the gelatinous mixture.

Second column: Total quantity of medicated injected material and of gelatinous mixture.

Third column: quantity of each ingredient in mg/uniform matrix of soft-gel for the newly formed matrix.

The last three columns refer to the situation after injection:

Fourth column: percentages of each ingredient in the newly formed matrix of soft-gel.

Fifth and sixth column: percentages of each ingredient in the dried matrix of soft-gel.

In the dried matrices (at a temperature between 20° C.-24° C. and relative humidity of 20% with a continuous change of the surrounding air until a constant weight is obtained, that is until two weighing operations carried out at an interval of 24 h do not differ by more than 1%) the weight is reduced on account of the almost complete elimination of water and ethanol which remain linked to the gelatine in the specified quantities.

|  | INITIAL | | | FINAL | | | |
|---|---|---|---|---|---|---|---|
|  | % | mg/matrix | Mg/matrix | Final composition % | | | |
| Medicated injected material | | | | | | | |
| Glycerol | 85.70 | 138.00 | 118.266 | 27.43481 | | | |
| Gelatine | 5.00 | 138.00 | 6.9 | 1.600631 | | | |
| Water | 9.00 | 138.00 | 12.42 | 2.881136 | | | |
| T4 | 0.30 | 138.00 | 0.414 | 0.096038 | 0.096038 | 0.1 | |
| Gelatinous mixture | | | | | | | |
| Gelatine | 42 | 470.00 | 197.4 | 45.79196 | 42.6926 | 42.7 | |
| Glycerol | 23 | 470.00 | 108.1 | 25.07655 | 52.51137 | 52.5 | |
| Water | 35 | 470.00 | 164.5 | 38.15997 | 4.7 | 4.7 | |
| Weight of uniform matrix of soft-gel | | | 608 | 431.08 | | | |

1.2

|  | INITIAL | | | FINAL | | | |
|---|---|---|---|---|---|---|---|
|  | % | mg/matrix | Mg/matrix | Final composition % | | | |
| Medicated injected material | | | | | | | |
| Glycerol | 64.70 | 50.00 | 32.35 | 9.500734 | | | |
| Gelatine | 5.00 | 50.00 | 2.5 | 0.734214 | | | |
| Water | 30.00 | 50.00 | 15 | 4.405286 | | | |
| T4 | 0.30 | 50.00 | 0.15 | 0.044053 | 0.044053 | 0.045 | |
| Gelatinous mixture | | | | | | | |
| Gelatine | 42 | 470.00 | 197.4 | 57.97357 | 52.90778 | 52.9 | |
| Glycerol | 23 | 470.00 | 108.1 | 31.74743 | 41.24816 | 41.25 | |
| Water | 35 | 470.00 | 164.5 | 48.31131 | 5.8 | 5.8 | |
| Weight of uniform matrix of soft-gel | | | 520 | 340.5 | | | |

1.3

|  | INITIAL | | | FINAL | | | |
|---|---|---|---|---|---|---|---|
|  | % | mg/matrix | Mg/matrix | Final composition % | | | |
| Medicated injected material | | | | | | | |
| Glycerol | 64.70 | 50.00 | 32.35 | 9.500734 | | | |
| Gelatine | 5.00 | 50.00 | 2.5 | 0.734214 | | | |
| Ethanol | 30.00 | 50.00 | 15 | 4.405286 | 2.00 | 2.0 | |
| T4 | 0.30 | 50.00 | 0.15 | 0.044053 | 0.044053 | 0.045 | |
| Gelatinous mixture | | | | | | | |
| Gelatine | 42 | 470.00 | 197.4 | 57.97357 | 52.70778 | 52.7 | |
| Glycerol | 23 | 470.00 | 108.1 | 31.74743 | 41.24816 | 41.25 | |
| Water | 35 | 470.00 | 164.5 | 48.31131 | 4.00 | 4.0 | |
| Weight of uniform matrix of soft-gel | | | 520 | 340.5 | | | |

Example 2

The following formulae were obtained according to the first procedure concerning the first aspect of the present invention.

| Gelatine | 56.58% | 56.60% | 60.55% |
|---|---|---|---|
| Glycerol | 37.07% | 37.09% | 32.68% |
| T4 | 0.06% | 0.023% | 0.029% |
| Water | 6.29% | 6.287% | 6.741% |

Example 3

The following formulae concern the second aspect of the present invention and were obtained according to the second procedure of the present invention:

The first three columns refer to the initial situation, that is before injection:

First column: percentage composition of the medicated injected material and of the gelatinous mixture.

Second column: Total quantity of medicated injected material and of gelatinous mixture.

Third column: quantity of each ingredient in mg/uniform matrix of soft-gel for the newly formed matrix.

The last three columns refer to the situation after injection:

Fourth column: percentages of each ingredient in the newly formed matrix of soft-gel.

Fifth and sixth column: percentages of each ingredient in the dried matrix of soft-gel.

In the dried matrices (at a temperature between 20° C.-24° C. and relative humidity of 20% with a continuous change of the surrounding air until a constant weight is obtained, that is until two weighing operations carried out at an interval of 24 h do not differ by more than 1%) the weight is reduced on account of the almost complete elimination of water and ethanol which remain linked to the gelatine in the specified quantities.

|  | INITIAL | | | FINAL | | |
|---|---|---|---|---|---|---|
|  | % | mg/matrix | Mg/matrix | Final composition % | | |
| Medicated injected material | | | | | | |
| Glycerol | 50.00 | 20.00 | 10 | 4.54 | 4.54 | 4.5 |
| Gelatine | 35.00 | 20.00 | 7 | 3.18 | | |
| Water | 10.00 | 20.00 | 2 | 0.91 | | |
| T4 | 0.30 | 20.00 | 0.06 | 0.03 | 0.03 | 0.027 |
| Gelatinous mixture | | | 0 | 0.00 | | |
| Gelatine | 42 | 330.00 | 138.6 | 52.95 | 56.80 | 56.8 |
| sorbitol/sorbitans 85% | 23 | 330.00 | 75.9 | 34.47 | 29.30 | 29.3 |
| Water | 35 | 330.00 | 115.5 | 52.46 | | 9.373 |
| Weight of uniform matrix (mg) | | | 349.06 | 220.175 | | 100 |

|  | INITIAL | | | FINAL | | |
|---|---|---|---|---|---|---|
|  | % | mg/matrix | Mg/matrix | Final composition % | | |
| Medicated injected material | | | | | | |
| Glycerol | 48.00 | 50.00 | 24 | 9.81 | 9.81 | 9.8 |
| Gelatine | 35.00 | 50.00 | 17.5 | 7.15 | | |
| Water | 10.00 | 50.00 | 5 | 2.04 | | |
| T4 | 0.30 | 50.00 | 0.15 | 0.06 | 0.06 | 0.061 |
| Gelatinous mixture | | | 0 | 0.00 | | |
| Gelatine | 42 | 330.00 | 138.6 | 56.63 | 57.40 | 57.2 |
| Sorbitol/sorbitans 85% | 23 | 330.00 | 75.9 | 31.01 | 26.36 | 26.2 |
| Water | 35 | 330.00 | 115.5 | 47.19 | | 5.739 |
| Weight of uniform matrix (mg) | | | 376.65 | 244.765 | | 100 |

|  | INITIAL | | | FINAL | | |
|---|---|---|---|---|---|---|
|  | % | mg/matrix | Mg/matrix | Final composition % | | |
| Medicated injected material | | | | | | |
| Glycerol | 50.00 | 20.00 | 10 | 5.85 | 5.85 | 5.9 |
| Gelatine | 35.00 | 20.00 | 7 | 4.10 | | |
| Water | 10.00 | 20.00 | 2 | 1.17 | | |
| T4 | 0.30 | 20.00 | 0.06 | 0.04 | 0.04 | 0.04 |
| Gelatinous mixture | | | 0 | 0.00 | | |
| Gelatine | 42 | 250.00 | 105 | 61.43 | 58.97 | 59 |
| Sorbitol/sorbitans 85% | 23 | 250.00 | 57.5 | 33.64 | 28.59 | 28.6 |
| Water | 35 | 250.00 | 87.5 | 51.19 | | 6.46 |
| Weight of uniform matrix (mg) | | | 269.06 | 170.935 | | 100 |

-continued

|  | INITIAL | | FINAL | | | |
|---|---|---|---|---|---|---|
|  | % | mg/matrix | Mg/matrix | Final composition % | | |
| Medicated injected material | | | | | | |
| Glycerol | 29.75 | 60.00 | 17.85 | 9.25 | 9.25 | 9.25 |
| Gelatine | 35.00 | 60.00 | 21 | 10.89 | | |
| Water | 35.25 | 60.00 | 21.15 | 10.96 | | |
| T4 | 0.30 | 60.00 | 0.18 | 0.09 | 0.09 | 0.09 |
| Gelatinous mixture | | | 0 | 0.00 | | |
| Gelatine | 42 | 250.00 | 105 | 54.43 | 58.79 | 58.8 |
| Sorbitol/sorbitans 85% | 23 | 250.00 | 57.5 | 29.81 | 25.34 | 25.3 |
| Water | 35 | 250.00 | 87.5 | 45.36 | | 6.56 |
| Weight of uniform matrix (mg) | | | 310.18 | 192.905 | | 100 |

|  | INITIAL | | FINAL | | | |
|---|---|---|---|---|---|---|
|  | % | mg/matrix | Mg/matrix | Final composition % | | |
| Medicated injected material | | | | | | |
| Glycerol | 27.75 | 150.00 | 41.625 | 9.80 | 9.80 | 9.8 |
| Gelatine | 50.00 | 150.00 | 75 | 17.65 | | |
| Water | 27.25 | 150.00 | 40.875 | 9.62 | | |
| T4 | 0.30 | 150.00 | 0.45 | 0.11 | 0.11 | 0.11 |
| Gelatinous mixture | | | 0 | 0.00 | | |
| Gelatine | 42 | 500.00 | 210 | 49.43 | 60.38 | 60.4 |
| Sorbitol/sorbitans 85% | 23 | 500.00 | 115 | 27.07 | 23.01 | 23 |
| Water | 35 | 500.00 | 175 | 41.19 | | 6.69 |
| Weight of uniform matrix (mg) | | | 657.95 | 424.825 | | 100 |

|  | INITIAL | | FINAL | | | |
|---|---|---|---|---|---|---|
|  | % | mg/matrix | Mg/matrix | Final composition % | | |
| Medicated injected material | | | | | | |
| Glycerol | 85.00 | 20.00 | 17 | 7.72 | 7.72 | 7.7 |
| Gelatine | 0.00 | 20.00 | 0 | 0.00 | | |
| Water | 15.00 | 20.00 | 3 | 1.36 | | |
| T4 | 0.30 | 20.00 | 0.06 | 0.03 | 0.03 | 0.03 |
| Gelatinous mixture | | | 0 | 0.00 | | |
| Gelatine | 42 | 330.00 | 138.6 | 62.95 | 56.65 | 56.7 |
| Sorbitol/sorbitans 85% | 23 | 330.00 | 75.9 | 34.47 | 29.30 | 29.3 |
| Water | 35 | 330.00 | 115.5 | 52.46 | | 6.27 |
| Weight of uniform matrix (mg) | | | 350.06 | 220.175 | | 100 |

|  | INITIAL | | FINAL | | | |
|---|---|---|---|---|---|---|
|  | % | mg/matrix | Mg/matrix | Final composition % | | |
| Medicated injected material | | | | | | |
| Glycerine | 85.00 | 20.00 | 17 | 8.00 | 8.00 | 8 |
| Gelatine | 0.00 | 20.00 | 0 | 0.00 | | |
| Water | 15.00 | 20.00 | 3 | 1.41 | | |
| T4 | 0.30 | 20.00 | 0.06 | 0.03 | 0.03 | 0.03 |
| Gelatinous mixture | | | 0 | 0.00 | | |
| Gelatine | 38 | 330.00 | 125.4 | 58.99 | 53.09 | 53.1 |
| Sorbitol/sorbitans 85% | 25 | 330.00 | 82.5 | 38.81 | 32.99 | 33 |
| Water | 37 | 330.00 | 122.1 | 57.44 | | 5.87 |
| Weight of uniform matrix (mg) | | | 350.06 | 212.585 | | 100 |

-continued

|  | INITIAL | | FINAL | |
|---|---|---|---|---|
|  | % | mg/matrix | Mg/matrix | Final composition % |
| Medicated injected material | | | | |
| Glycerol | 57.00 | 20.00 | 11.4 | 9.90 | 9.90 |
| Gelatine | 0.00 | 20.00 | 0 | 0.00 | |
| Water | 43.00 | 20.00 | 8.6 | 7.47 | |
| T4 | 0.30 | 20.00 | 0.06 | 0.05 | 0.05 |
| Gelatinous mixture | | | 0 | 0.00 | |
| Gelatine | 38 | 175.00 | 66.5 | 57.75 | 51.98 |
| Sorbitol/sorbitans 85% | 25 | 175.00 | 43.75 | 37.99 | 32.30 |
| Water | 37 | 175.00 | 64.75 | 56.23 | |
| Weight of uniform matrix (mg) | | | 195.06 | 115.1475 | |

Example 4

The following formulae were obtained according to the first procedure concerning the second aspect of the present invention. The initial composition refers to before drying, while the final composition refers to after drying according to the conditions defined above (at a temperature between 20° C.-24° C. and relative humidity of 20% with a continuous change of the surrounding air until a constant weight is obtained, that is until two weighing operations carried out at an interval of 24 h do not differ by more than 1%).

|  | INITIAL | | FINAL | |
|---|---|---|---|---|
|  | % | mg/matrix | Mg/matrix | Final composition % |
| Medicated Gelatinous material | | | 0 | | |
| Gelatine | 42 | 330.00 | 138.6 | 59.47 | 59.5 |
| Sorbitol/sorbitans 85% | 23 | 330.00 | 75.9 | 30.76 | 30.8 |
| Glycerine | 2 | 330.00 | 6.6 | 3.15 | 3.1 |
| T4 | 0.0075 | 330.00 | 0.02475 | | 0.012 |
| Water | 33 | 330.00 | 108.9 | | 6.6 |
| Weight of uniform matrix (mg) | | | 330.0 | 209.7 | 100 |

|  | INITIAL | | FINAL | |
|---|---|---|---|---|
|  | % | mg/matrix | Mg/matrix | Final composition % |
| Medicated Gelatinous material | | | 0 | | |
| Gelatine | 38 | 330.00 | 125.4 | 56.48 | 56.5 |
| Sorbitol/sorbitans 85% | 23 | 330.00 | 75.9 | 32.28 | 32.3 |
| Glycerine | 3 | 330.00 | 9.9 | 4.95 | 5 |
| T4 | 0.0075 | 330.00 | 0.02475 | | 0.013 |
| Water | 36 | 330.00 | 118.8 | | 6.187 |
| Weight of uniform matrix (mg) | | | 330.0 | 199.8 | 100 |

|  | INITIAL | | FINAL | |
|---|---|---|---|---|
|  | % | mg/matrix | Mg/matrix | Final composition % |
| Medicated Gelatinou material | | | 0 | | |
| Gelatine | 38 | 330.00 | 125.4 | 58.37 | 58.4 |
| Sorbitol/sorbitans 85% | 23 | 330.00 | 75.9 | 33.36 | 33.4 |
| Glycerine | 1 | 330.00 | 3.3 | 1.71 | 1.7 |
| T4 | 0.046 | 330.00 | 0.1518 | | 0.013 |
| Water | 38 | 330.00 | 125.4 | | 6.487 |
| Weight of uniform matrix (mg) | | | 330.2 | 193.4 | 100 |

-continued

|  | INITIAL | | | FINAL | |
|---|---|---|---|---|---|
|  | % | mg/matrix | Mg/matrix |  | Final composition % |
| Medicated Gelatinou material |  |  | 0 |  |  |
| Gelatine | 38 | 330.00 | 125.4 | 62.24 | 62.2 |
| Sorbitol/sorbitans 85% | 14 | 330.00 | 46.2 | 21.66 | 21.7 |
| Glycerine | 5 | 330.00 | 16.5 | 9.10 | 9.1 |
| T4 | 0.046 | 330.00 | 0.1518 |  | 0.08 |
| Water | 43 | 330.00 | 141.9 |  | 6.92 |
| Weight of uniform matrix (mg) |  |  | 330.2 | 181.3 | 100 |

|  | INITIAL | | | FINAL | |
|---|---|---|---|---|---|
|  | % | mg/matrix | Mg/matrix |  | Final composition % |
| Medicated Gelatinou material |  |  | 0 |  |  |
| Gelatine | 30 | 330.00 | 99 | 47.78 | 47.8 |
| Sorbitol/sorbitans 85% | 30 | 330.00 | 99 | 45.12 | 45.1 |
| Glycerine | 1 | 330.00 | 3.3 | 1.77 | 1.8 |
| T4 | 0.01 | 330.00 | 0.033 |  | 0.02 |
| Water | 39 | 330.00 | 128.7 |  | 5.28 |
| Weight of uniform matrix (mg) |  |  | 330.0 | 186.5 | 100 |

|  | INITIAL | | | FINAL | |
|---|---|---|---|---|---|
|  | % | mg/matrix | Mg/matrix |  | Final composition % |
| Medicated Gelatinou material |  |  | 0 |  |  |
| Gelatine | 24 | 330.00 | 79.2 | 35.21 | 35.1 |
| Sorbitol/sorbitans 85% | 38 | 330.00 | 125.4 | 52.65 | 52.7 |
| Glycerine | 5 | 330.00 | 16.5 | 8.15 | 8.1 |
| T4 | 0.046 | 330.00 | 0.1518 |  | 0.07 |
| Water | 33 | 330.00 | 108.9 |  | 4.03 |
| Weight of uniform matrix (mg) |  |  | 330.2 | 202.4 | 100 |

Example 5

Obtaining formulae for thyroid hormones in uniform matrices of soft-gel according to both aspects of the present invention, in particular according to the first variation of the first procedure:

Introduction, in a stainless steel reactor, equipped with a heating system, mixer and equipment for operating in a vacuum and under pressure, of a medicated gelatinous mixture as defined above; the mass thus obtained is brought to melting point around 50° C., stirring all the time and working in a vacuum. When it is completely melted the mixture is transferred to suitable thermostat-controlled stainless steel containers, where it is kept at about 45° C. From there, the mixture is fed into a "Rotary Die" type machine for forming capsules, for example a "MKSJ ENCAPSULATING MACHINE (SEN JIN SDN.BHD)".

In particular, the hot gelatinous mixture feeds two dosing devices on the machine, which form two gelatinous films of a determined and constant thickness on two air-cooled rollers. The two films pass through two capsule-shaping cylinders which turn concentrically, on top of which is a particular heated wedge, called injector segment, which is not used in this procedure. Passing through the cylinders, the capsule-shaping cavities form uniform matrices of soft-gel from the two gelatinous films. The cut uniform matrices of soft-gel fall below the shaping cylinders in rotating baskets from which, after staying there several hours, they are turned out onto trays for drying.

If starting from a non medicated gelatinous mixture, that is in the second variation of the first procedure, the procedure is similar, but the melting temperature is higher, around 65° C. When it is completely melted the mixture is transferred to suitable thermostat-controlled stainless steel containers, where it is kept at about 45° C. for the desired time. Then the medicated mixture is added, homogenised, and from there, preferably within one hour, the mixture is fed into a "Rotary Die" type machine for forming capsules, which completes the shaping of uniform matrices of soft-gel as described above with relation to the first variation of the first procedure.

Example 6

Obtaining formulae for thyroid hormones in uniform matrices of soft-gel according to both aspects of the present invention, in particular according to the second procedure:

the procedure corresponds to the second variation of the first procedure, without adding the medicated substance to the mixture before feeding it to the machine. The hot gelatinous mixture feeds two dosing devices on the machine, which form two gelatinous films of a determined and constant thickness on two air-cooled rollers. The two films pass through two capsule-shaping cylinders which turn concentrically, on top of which is a particular heated wedge, called the injector segment. The medicated injected substances is fed directly to a dosing pump that has precision syringes which, sliding alternately, feed the injector segment through small pipes, injecting a quantity of medicated injected substance into the gelatinous mixture contained in the cavities of the two shaping cylinders. The medicated injected substance spreads through the gelatinous mixture, thus forming the uniform matrices of soft-gel which are cut and fall below the shaping cylinders in rotating baskets from which, after staying there several hours, they are turned out onto trays for drying.

Example 7

The following compositions were obtained according to the first procedure concerning the first aspect of the invention (preparation without injection of a medicated solution; matrix with high glycerol content, sorbitol/sorbitans-free). The table displays the final composition in the dried state, as herein defined.

| | Composition % | | | | | | |
|---|---|---|---|---|---|---|---|
| | Batch | | | | | | |
| INGREDIENT | 100 | 104 | 116 | 127 | 130 | 133 | 134 |
| GELATIN | 61.1 | 56.59 | 59 | 59.25 | 58.89 | 59.25 | 58.89 |
| GLYCEROL | 32.3 | 37.069 | 35 | 34.95 | 34.73 | 34.95 | 34.73 |
| WATER | 6.5 | 6.309 | 6 | 5.75 | 5.72 | 5.75 | 5.72 |
| TITANIUM DIOXIDE | | | | | 0.60 | | 0.60 |
| T4 | 0.029 | 0.023 | 0.046 | 0.046 | 0.046 | 0.023 | 0.023 |

Stability Studies (According to ICH)

Respective stability studies were conducted according to ICH guide lines in two different packaging conditions 1.-Glass Bottles Stability studies were carried out in glass bottles with a stopper including silica gel, in order to guarantee the highest moisture barrier.

| | Stability data: 25° C./60% RH and 30° C./60% RH (% of drug substance) | | | | | | | | | | | | | |
|---|---|---|---|---|---|---|---|---|---|---|---|---|---|---|
| | 25° C.-60% RH | | | | | | | 30° C.-60% RH | | | | | | |
| TIME | BATCH | | | | | | | | | | | | | |
| (days) | 100 | 104 | 116 | 127 | 130 | 133 | 134 | 100 | 104 | 116 | 127 | 130 | 133 | 134 |
| Initial | 100.00 | 100.00 | 100.00 | 100.00 | 100.00 | 100.00 | 100.00 | 100.00 | 100.00 | 100.00 | 100.00 | 100.00 | 100.00 | 100.00 |
| 30 | 94.60 | 98.63 | 94.86 | — | — | 94.16 | 99.17 | 93.50 | 98.44 | 97.38 | 103.44 | 96.87 | 91.43 | 96.17 |
| 60 | 97.50 | 96.43 | 94.11 | — | — | — | — | 96.60 | 92.77 | 94.29 | | | 92.21 | 100.62 |
| 90 | 93.80 | 95.70 | 97.10 | 104.50 | 94.13 | 99.81 | 99.69 | 92.60 | 92.50 | 94.95 | 95.95 | 101.96 | 97.86 | 99.59 |
| 180 | 96.60 | 97.53 | 98.32 | 99.19 | 99.71 | 94.06 | 91.75 | 95.20 | 95.79 | 94.76 | 97.16 | 95.89 | 89.48 | 97.62 |
| 270 | 96.30 | 100.00 | 96.28 | | | | | | | | | | | |
| 360 | 94.30 | | | | | | | | | | | | | |

2.-Blister

For the blisters packaging, 2 different types of plastic materials have been tested: bilayer PVC-PVDC and PENTAPHARM ACLAR®.

The stability controls carried out on development batches yield good results with no significant differences between both kind of plastic materials: coupled PVC-PVDC and ACLAR

| | Stability data: 25° C.-60% RH (% of drug substance) | | | | | | | | | |
|---|---|---|---|---|---|---|---|---|---|---|
| | PVDC | | | | | ACLAR | | | | |
| TIME | BATCH | | | | | | | | | |
| (days) | 100 | 116 | 127 | 133 | 134 | 104 | 116 | 127 | 133 | 134 |
| Initial | 100.00 | 100.00 | 98.7 | 100.00 | 100.00 | 100.00 | 100.00 | 100.00 | 100.00 | 100.00 |
| 30 | 96.50 | 97.44 | — | 95.42 | 97.41 | 99.63 | 97.42 | | 95.33 | 97.62 |
| 60 | 97.00 | 97.35 | — | | | 95.33 | 99.62 | | | |
| 90 | 98.50 | 97.25 | 103 | 99.32 | 99.48 | 93.41 | 99.71 | 98.58 | 98.73 | 98.96 |

-continued

Stability data: 25° C.-60% RH (% of drug substance)

| TIME | PVDC | | | | | ACLAR | | | | |
|---|---|---|---|---|---|---|---|---|---|---|
| | BATCH | | | | | | | | | |
| (days) | 100 | 116 | 127 | 133 | 134 | 104 | 116 | 127 | 133 | 134 |
| 180 | 94.80 | 91.75 | | 92.02 | 96.89 | 94.78 | 98.57 | 98.48 | 92.41 | 95.96 |
| 270 | | 97.44 | | | | | 97.71 | 97.90 | | |
| 360 | 92.20 | | | | | | | | | |

Stability data: 30° C.-60% RH (% of drug substance)

| TIME | PVDC | | | | | ACLAR | | | | |
|---|---|---|---|---|---|---|---|---|---|---|
| | BATCH | | | | | | | | | |
| (days) | 116 | 127 | 130 | 133 | 134 | 116 | 127 | 130 | 133 | 134 |
| Initial | 100.00 | 100.00 | 100.00 | 100.00 | 100.00 | 100.00 | 98.7 | 102.3 | 102.7 | 96.6 |
| 30 | 96.87 | 102.94 | 100.3 | 93.57 | 97.1 | 96.76 | 102.23 | 97.94 | 92.31 | 97.62 |
| 60 | 96.02 | — | — | — | — | 97.52 | — | — | — | — |
| 90 | 97.91 | 101.82 | 100.1 | 97.17 | 97.22 | 98.09 | 96.05 | 96.28 | 96.11 | 97.1 |
| 180 | 95.92 | | | | | 98.09 | 98.28 | 96.28 | | 90.79 |
| 270 | | | | | | | | | | |
| 360 | | | | | | | | | | |

Example 8

The following compositions were obtained according to the second procedure concerning the first aspect of the invention (manufacture through injection of medicated solution which spreads uniformly across the matrix without affecting the single-phase structure thereof; matrix with high glycerol content; sorbitol/sorbitans-free). The table displays the final composition in the dried state, as herein defined.

Batches 141/IB-79, 142/IB-79 and 143/IB-79 Composition for Levothyroxine soft gelatin matrices 12.5 µg

| Name of the components | Percent formula (w/w) | Unitary amount mg/sgm |
|---|---|---|
| Active ingredient | | |
| Sodium Levothyroxine | 0.0061 | 0.0125 |
| Excipients | | |
| Hydrolyzed gelatin | 8.5366 | 17.5 |
| Gelatin 80 bloom | 1.2195 | 2.5 |
| Glycerol 85% | 8.5366 | 17.5 |
| Anhydrous Glycerol | 28.0488 | 57.5 |
| Gelatin 150 Bloom | 47.5610 | 97.5 |
| Purified Water | 6.0915 | 12.488 |
| Total | 100.0000 | 205.0000 |

Batch 144/IB-79 Composition for Levothyroxine soft gelatin matrices 25 µg

| Name of the components | Percent formula (w/w) | Unitary amount mg/sgm |
|---|---|---|
| Active ingredient | | |
| Sodium Levothyroxine | 0.0122 | 0.025 |
| Excipients | | |
| Hydrolyzed gelatin | 8.5366 | 17.5 |
| Gelatin 80 bloom | 1.2195 | 2.5 |
| Glycerol 85% | 8.5366 | 17.5 |
| Anhydrous Glycerol | 28.0488 | 57.5 |
| Gelatin 150 Bloom | 47.5610 | 97.5 |
| Purified Water | 6.0854 | 12.475 |
| Total | 100.0000 | 205.0000 |

Batch 145/IB-79 Composition for Levothyroxine soft gelatin matrices 50 µg

| Name of the components | Percent formula (w/w) | Unitary amount mg/sgm |
|---|---|---|
| Active ingredient | | |
| Sodium Levothyroxine | 0.0244 | 0.05 |
| Excipients | | |
| Hydrolyzed gelatin | 8.5366 | 17.5 |
| Gelatin 80 bloom | 1.2195 | 2.5 |
| Glycerol 85% | 8.5366 | 17.5 |
| Anhydrous Glycerol | 28.0488 | 57.5 |

Batch 145/IB-79 Composition for Levothyroxine soft gelatin matrices 50 μg

| Name of the components | Percent formula (w/w) | Unitary amount mg/sgm |
|---|---|---|
| Gelatin 150 Bloom | 47.5610 | 97.5 |
| Purified Water | 6.0732 | 12.450 |
| Total | 100.0000 | 205.0000 |

Batches 146/IB-79, 147/IB-79, 148/IB-79 Composition for Levothyroxine soft gelatin matrices 75 μg

| Name of the components | Percent formula (w/w) | Unitary amount mg/sgm |
|---|---|---|
| Active ingredient | | |
| Sodium Levothyroxine | 0.0366 | 0.075 |
| Excipients | | |
| Hydrolyzed gelatin | 8.5366 | 17.5 |
| Gelatin 80 bloom | 1.2195 | 2.5 |
| Glycerol 85% | 8.5366 | 17.5 |
| Anhydrous Glycerol | 28.0488 | 57.5 |
| Gelatin 150 Bloom | 47.5610 | 97.5 |
| Purified Water | 6.0610 | 12.425 |
| Total | 100.0000 | 205.0000 |

Batch 136/IB-79 Composition for Levothyroxine soft gelatin matrices 100 μg

| Name of the components | Percent formula (w/w) | Unitary amount mg/sgm |
|---|---|---|
| Active ingredient | | |
| Sodium Levothyroxine | 0.0488 | 0.1 |
| Excipients | | |
| Hydrolyzed gelatin | 8.5366 | 17.5 |
| Gelatin 80 bloom | 1.2195 | 2.5 |
| Glycerol 85% | 8.5366 | 17.5 |
| Anhydrous Glycerol | 28.0488 | 57.5 |
| Gelatin 150 Bloom | 47.5610 | 97.5 |
| Purified Water | 6.0488 | 12.400 |
| Total | 100.0000 | 205.0000 |

Batch 149/IB-79 Composition for Levothyroxine soft gelatin matrices 125 μg

| Name of the components | Percent formula (w/w) | Unitary amount mg/sgm |
|---|---|---|
| Active ingredient | | |
| Sodium Levothyroxine | 0.0610 | 0.125 |
| Excipients | | |
| Hydrolyzed gelatin | 8.5366 | 17.5 |
| Gelatin 80 bloom | 1.2195 | 2.5 |
| Glycerol 85% | 8.5366 | 17.5 |
| Anhydrous Glycerol | 28.0488 | 57.5 |
| Gelatin 150 Bloom | 47.5610 | 97.5 |
| Purified Water | 6.0366 | 12.375 |
| Total | 100.0000 | 205.0000 |

Batches 150/IB-79, 151/IB-79, 152/IB-79 Composition for Levothyroxine soft gelatin matrices 150 μg

| Name of the components | Percent formula (w/w) | Unitary amount mg/sgm |
|---|---|---|
| Active ingredient | | |
| Sodium Levothyroxine | 0.0732 | 0.15 |
| Excipients | | |
| Hydrolyzed gelatin | 8.5366 | 17.5 |
| Gelatin 80 bloom | 1.2195 | 2.5 |
| Glycerol 85% | 8.5366 | 17.5 |
| Anhydrous Glycerol | 28.0488 | 57.5 |
| Gelatin 150 Bloom | 47.5610 | 97.5 |
| Purified Water | 6.0244 | 12.350 |
| Total | 100.0000 | 205.0000 |

Example 9

With the formulations according to example 8, stability testing was conducted as specified herein below:

T4 Soft-gel matrices - Batch N° 141/IB-79, dosage: 12.5 μg; manufactured February 2003 - start stability March 2003 - contained in glass flacon

| Test | Stability specifications | T0 | 3 months 30° C. ± 2° C./ 60% ± 5% R.H. | 3 months 25° C. ± 2° C./ 60% ± 5% R.H. | 6 months 30° C. ± 2° C./ 60% ± 5% R.H. | 6 months 25° C. ± 2° C./ 60% ± 5% R.H. |
|---|---|---|---|---|---|---|
| Characters | round biconvex matrices, amber-coloured | complies | complies | complies | complies | complies |

-continued

T4 Soft-gel matrices - Batch N° 141/IB-79, dosage: 12.5 µg; manufactured February 2003 - start stability March 2003 - contained in glass flacon

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Degradation product ($T_3$ content) | ≦4% | 0.2% | 0.4% * | 0.4% * | <LOD (LOD = 1.4%) | <LOD (LOD = 1.4%) |
| Average assay | 90-110% of the theoretical value | 96.7% | 96.2% * | 96.4% * | 95.6% * | 95.8% * |
| Average weight | 205.0 mg ± 10% | 198.1 mg | 197.7 mg | 200.2 mg | 196.6 mg | 195.9 mg |
| Dissolution test | ≧70% in 45 minutes | complies | not performed | not performed | not performed | not performed |
| Microbial controls: | Aerobic bacteria: ≦1000 CFU/g Moulds and yeasts: ≦100 CFU/g *Escherichia Coli*: absent/g | complies: 65 CFU/g <5 CFU/g absent/g | not performed | not performed | not performed | not performed |

* of the theoretical value

T4 Soft gel matrices - Batch N° 141/IB-79, dosage: 12.5 µg; manufactured February 2003 - start stability March 2003 - contained in blister ACCLAR

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.2% | 0.3% * | 0.3% * | <LOD (LOD = 1.4%) | <LOD (LOD = 1.4%) |
| Average assay | 90-110% of the theoretical value | 96.7% | 96.0% * | 96.2% * | 95.6% * | 95.8% * |
| Average weight | 205.0 mg ± 10% | 198.1 mg | 198.8 mg | 199.8 mg | 198.8 mg | 199.4 mg |
| Dissolution test | ≧70% in 45 minutes | complies | not performed | not performed | not performed | not performed |
| Microbial controls: | Aerobic bacteria: ≦1000 CFU/g Moulds and yeasts: ≦100 CFU/g *Escherichia Coli*: absent/g | complies: 65 CFU/g <5 CFU/g absent/g | not performed | not performed | not performed | not performed |

* of the theoretical value

T4 Soft gel matrices - Batch N° 142/IB-79, dosage: 12.5 µg; manufactured March 2003 - start stability March 2003 - contained in glass flacon

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.2% | 0.5% * | 0.6% * | <LOD (LOD = 1.4%) | <LOD (LOD = 1.4%) |
| Average assay | 90-110% of the theoretical value | 95.4% | 94.9% * | 95.3% * | 94.8% * | 95.0% * |

-continued

T4 Soft gel matrices - Batch N° 142/IB-79, dosage: 12.5 μg; manufactured
March 2003 - start stability March 2003 - contained in glass flacon

| | | | 3 months | | 6 months | |
| --- | --- | --- | --- | --- | --- | --- |
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Average weight | 205.0 mg ± 10% | 196.3 mg | 201.3 mg | 199.6 mg | 195.6 mg | 196.8 mg |
| Dissolution test | ≧70% in 45 minutes | complies | not performed | not performed | | not performed |
| Microbial controls: | Aerobic bacteria: ≦1000 CFU/g Moulds and yeasts: ≦100 CFU/g *Escherichia Coli*: absent/g | complies: 40 CFU/g <5 CFU/g absent/g | not performed | not performed | | not performed |

* of the theoretical value

T4 Soft gel matrices - Batch N° 142/IB-79, dosage: 12.5 μg; manufactured
March 2003 - start stability March 2003 - contained in blister ACCLAR

| | | | 3 months | | 6 months | |
| --- | --- | --- | --- | --- | --- | --- |
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.2% | 0.4% * | 0.4% * | <LOD (LOD = 1.4%) | <LOD (LOD = 1.4%) |
| Average assay | 90-110% of the theoretical value | 95.4% | 94.8% * | 95.4% * | 93.5 * | 95.1 * |
| Average weight | 205.0 mg ± 10% | 196.3 mg | 200.0 mg | 200.7 mg | 197.8 mg | 197.5 mg |
| Dissolution test | ≧70% in 45 minutes | complies | not performed | not performed | | not performed |
| Microbial controls: | Aerobic bacteria: ≦1000 CFU/g Moulds and yeasts: ≦100 CFU/g *Escherichia Coli*: absent/g | complies: 40 CFU/g <5 CFU/g absent/g | not performed | not performed | | not performed |

* of the theoretical value

T4 Soft gel matrices - Batch N° 143/IB-79, dosage: 12.5 μg; manufactured
March 2003 - start stability March 2003 - contained in glass flacon

| | | | 3 months | | 6 months | |
| --- | --- | --- | --- | --- | --- | --- |
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.4% | 0.5% * | 0.5% * | <LOD (LOD = 1.4%) | <LOD (LOD = 1.4%) |
| Average assay | 90-110% of the theoretical value | 94.4% | 94.1% * | 94.3% * | 93.5% * | 94.2% * |
| Average weight | 205.0 mg ± 10% | 197.6 mg | 200.8 mg | 200.9 mg | 197.8 mg | 199.3 mg |
| Dissolution test | ≧70% in 45 minutes | complies | not performed | not performed | | not performed |
| Microbial controls: | Aerobic bacteria: ≦1000 CFU/g | complies: 35 CFU/g <5 CFU/g absent/g | not performed | not performed | | not performed |

-continued

T4 Soft gel matrices - Batch N° 143/IB-79, dosage: 12.5 μg; manufactured March 2003 - start stability March 2003 - contained in glass flacon

| Test | Stability specifications | T0 | 3 months 30° C. ± 2° C./ 60% ± 5% R.H. | 3 months 25° C. ± 2° C./ 60% ± 5% R.H. | 6 months 30° C. ± 2° C./ 60% ± 5% R.H. | 6 months 25° C. ± 2° C./ 60% ± 5% R.H. |
|---|---|---|---|---|---|---|
| | Moulds and yeasts: ≦100 CFU/g *Escherichia Coli*: absent/g | | | | | |

* of the theoretical value

T4 Soft gel matrices - Batch N° 143/IB-79, dosage: 12.5 μg; manufactured March 2003 - start stability March 2003 - contained in blister ACCLAR

| Test | Stability specifications | T0 | 3 months 30° C. ± 2° C./ 60% ± 5% R.H. | 3 months 25° C. ± 2° C./ 60% ± 5% R.H. | 6 months 30° C. ± 2° C./ 60% ± 5% R.H. | 6 months 25° C. ± 2° C./ 60% ± 5% R.H. |
|---|---|---|---|---|---|---|
| Characters | round biconvex matrices, amber-coloured | complies | complies | complies | complies | complies |
| Degradation product ($T_3$ content) | ≦4% | 0.4% | 0.4% * | 0.4% * | <LOD (LOD = 1.4%) | <LOD (LOD = 1.4%) |
| Average assay | 90-110% of the theoretical value | 94.4% | 94.0% * | 94.3% * | 93.5% * | 94.0% * |
| Average weight | 205.0 mg ± 10% | 197.6 mg | 202.7 mg | 201.4 mg | 198.1 mg | 198.8 mg |
| Dissolution test | ≧70% in 45 minutes | complies | not performed | not performed | | not performed |
| Microbial controls: | Aerobic bacteria: ≦1000 CFU/g Moulds and yeasts: ≦100 CFU/g *Escherichia Coli*: absent/g | complies: 35 CFU/g <5 CFU/g absent/g | not performed | not performed | | not performed |

* of the theoretical value

T4 Soft gel matrices - Batch N° 144/IB-79, dosage: 25 μg; manufactured March 2003 - start stability March 2003 - contained in glass flacon

| Test | Stability specifications | T0 | 3 months 30° C. ± 2° C./ 60% ± 5% R.H. | 3 months 25° C. ± 2° C./ 60% ± 5% R.H. | 6 months 30° C. ± 2° C./ 60% ± 5% R.H. | 6 months 25° C. ± 2° C./ 60% ± 5% R.H. |
|---|---|---|---|---|---|---|
| Characters | round biconvex matrices, amber-coloured | complies | complies | complies | complies | complies |
| Degradation product ($T_3$ content) | ≦4% | 0.8% | 0:3% * | 0.4% * | <LOD (LOD = 1.4%) | <LOD (LOD = 1.4%) |
| Average assay | 90-110% of the theoretical value | 91.8% | 90.8% * | 91.0% * | 89.5% * | 90.5% * |
| Average weight | 205.0 mg ± 10% | 203.0 mg | 206.7 mg | 207.2 mg | 202.4 mg | 200.0 mg |
| Dissolution test | ≧70% in 45 minutes | complies | not performed | not performed | | not performed |
| Microbial controls: | Aerobic bacteria: ≦1000 CFU/g Moulds and yeasts: ≦100 CFU/g *Escherichia Coli*: absent/g | complies: 60 CFU/g <5 CFU/g absent/g | not performed | not performed | | not performed |

* of the theoretical value

T4 Soft gel matrices - Batch N° 144/IB-79, dosage: 25 μg; manufactured March 2003 - start stability March 2003 - contained in blister ACCLAR

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies. | complies |
| Degradation product ($T_3$ content) | ≦4% | 0.8% | 0.4% * | 0.4% * | <LOD (LOD = 1.4%) | <LOD (LOD = 1.4%) |
| Average assay | 90-110% of the theoretical value | 91.8% | 91.3% * | 91.6% * | 91.0% * | 91.4% * |
| Average weight | 205.0 mg ± 10% | 203.0 mg | 205.4 mg | 206.5 mg | 204.1 mg | 204.5 mg |
| Dissolution test | ≧70% in 45 minutes | complies | not performed | not performed | | not performed |
| Microbial controls: | Aerobic bacteria: ≦1000 CFU/g Moulds and yeasts: ≦100 CFU/g *Escherichia Coli*: absent/g | complies: 60 CFU/g <5 CFU/g absent/g | not performed | not performed | | not performed |

* of the theoretical value

T4 Soft gel matrices - Batch N° 145/IB-79, dosage: 50 μg; manufactured March 2003 - start stability March 2003 - contained in glass flacon

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.3% | 0.3% * | 0.3% * | <LOD (LOD = 1.4%) | <LOD (LOD = 1.4%) |
| Average assay | 90-110% of the theoretical value | 97.6% | 97.0% * | 97.0% * | 97.0% * | 97.5% * |
| Average weight | 205.0 mg ± 10% | 208.4 mg | 205.7 mg | 206.0 mg | 203.9 mg | 203.4 mg |
| Dissolution test | ≧70% in 45 minutes | complies | not performed | not performed | | not performed |
| Microbial controls: | Aerobic bacteria: ≦1000 CFU/g Moulds and yeasts: ≦100 CFU/g *Escherichia Coli*: absent/g | complies: 35 CFU/g <5 CFU/g absent/g | not performed | not performed | | not performed |

* of the theoretical value

T4 Soft gel matrices - Batch N° 145/IB-79, dosage: 50 μg; manufactured March 2003 - start stability March 2003 - contained in blister ACCLAR

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |

-continued

T4 Soft gel matrices - Batch N° 145/IB-79, dosage: 50 μg; manufactured March 2003 - start stability March 2003 - contained in blister ACCLAR

| Test | Stability specifications | T0 | 3 months 30° C. ± 2° C./ 60% ± 5% R.H. | 3 months 25° C. ± 2° C./ 60% ± 5% R.H. | 6 months 30° C. ± 2° C./ 60% ± 5% R.H. | 6 months 25° C. ± 2° C./ 60% ± 5% R.H. |
|---|---|---|---|---|---|---|
| Degradation product ($T_3$ content) | ≦4% | 0.3% | 0.4% * | 0.3% * | <LOD (LOD = 1.4%) | <LOD (LOD = 1.4%) |
| Average assay | 90-110% of the theoretical value | 97.6% | 96.7% * | 97.4% * | 95.0% * | 97.0% * |
| Average weight | 205.0 mg ± 10% | 208.4 mg | 205.3 mg | 205.7 mg | 204.6 mg | 202.3 mg |
| Dissolution test | ≧70% in 45 minutes | complies | not performed | not performed | | not performed |
| Microbial controls: | Aerobic bacteria: ≦1000 CFU/g Moulds and yeasts: ≦100 CFU/g *Escherichia Coli*: absent/g | complies: 35 CFU/g <5 CFU/g absent/g | not performed | not performed | not performed | not performed |

* of the theoretical value

T4 Soft gel matrices - Batch N° 146/IB-79, dosage: 75 μg; manufactured March 2003 - start stability March 2003 - contained in glass flacon

| Test | Stability specifications | T0 | 3 months 30° C. ± 2° C./ 60% ± 5% R.H. | 3 months 25° C. ± 2° C./ 60% ± 5% R.H. | 6 months 30° C. ± 2° C./ 60% ± 5% R.H. | 6 months 25° C. ± 2° C./ 60% ± 5% R.H. |
|---|---|---|---|---|---|---|
| Characters | round biconvex matrices, amber-coloured | complies | complies | complies | complies | complies |
| Degradation product ($T_3$ content) | ≦4% | 0.3% | 0.4% * | 0.3% * | < LOD (LOD = 0.9%) | < LOD (LOD = 0.9%) |
| Average assay | 90-110% of the theoretical value | 94.0% | 92.3% * | 93.9% * | 92.8% * | 92.4% * |
| Average weight | 205.0 mg ± 10% | 199.4 mg | 200.1 mg | 201.3 mg | 198.6 mg | 198.4 mg |
| Dissolution test | ≧70% in 45 minutes | complies | not performed | not performed | not performed | not performed |
| Microbial controls: | Aerobic bacteria: ≦1000 CFU/g Moulds and yeasts: ≦100 CFU/g *Escherichia Coli*: absent/g | complies: 25 CFU/g <5 CFU/g absent/g | not performed | not performed | not performed | not performed |

* of the theoretical value

T4 Soft gel matrices - Batch N° 146/IB-79, dosage: 75 μg; manufactured March 2003 - start stability March 2003 - contained in blister ACCLAR

| Test | Stability specifications | T0 | 3 months 30° C. ± 2° C./ 60% ± 5% R.H. | 3 months 25° C. ± 2° C./ 60% ± 5% R.H. | 6 months 30° C. ± 2° C./ 60% ± 5% R.H. | 6 months 25° C. ± 2° C./ 60% ± 5% R.H. |
|---|---|---|---|---|---|---|
| Characters | round biconvex matrices, amber-coloured | complies | complies | complies | complies | complies |
| Degradation product ($T_3$ content) | ≦4% | 0.3% | 0.4% * | 0.3% * | <LOD (LOD = 0.9%) | <LOD (LOD = 0.9%) |

-continued

T4 Soft gel matrices - Batch N° 146/IB-79, dosage: 75 μg; manufactured
March 2003 - start stability March 2003 - contained in blister ACCLAR

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Average assay | 90-110% of the theoretical value | 94.0% | 93.4% * | 93.9% * | 92.6% * | 93.5% * |
| Average weight | 205.0 mg ± 10% | 199.4 mg | 200.0 mg | 200.5 mg | 198.7 mg | 200.2 mg |
| Dissolution test | ≧70% in 45 minutes | complies | not performed | not performed | | not performed |
| Microbial controls: | Aerobic bacteria: ≦1000 CFU/g Moulds and yeasts: <100 CFU/g *Escherichia Coli*: absent/g | complies: 25 CFU/g <5 CFU/g absent/g | not performed | not performed | | not performed |

* of the theoretical value

T4 Soft gel matrices - Batch N° 147/IB-79, dosage: 75 μg; manufactured
March 2003 - start stability March 2003 - contained in glass flacon

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.2% | 0.4% * | 0.3% * | <LOD (LOD = 0.9%) | <LOD (LOD = 0.9%) |
| Average assay | 90-110% of the theoretical value | 94.9% | 90.6% * | 94.6% * | 93.5% * | 91.4% * |
| Average weight | 205.0 mg ± 10% | 201.5 mg | 201.0 mg | 201.6 mg | 198.4 mg | 199.9 mg |
| Dissolution test | ≧70% in 45 minutes | complies | not performed | not performed | | not performed |
| Microbial controls: | Aerobic bacteria: ≦1000 CFU/g Moulds and yeasts: <100 CFU/g *Escherichia Coli*: absent/g | complies: 10 CFU/g <5 CFU/g absent/g | not performed | not performed | | not performed |

* of the theoretical value

T4 Soft gel matrices - Batch N° 147/IB-79, dosage: 75 μg; manufactured
March 2003 - start stability March 2003 - contained in blister ACCLAR

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.2% | 0.3% * | 0.3% * | <LOD (LOD = 0.9%) | <LOD (LOD = 0.9%) |
| Average assay | 90-110% of the theoretical value | 94.9% | 92.0% * | 94.1% * | 92.1% * | 93.3% * |
| Average weight | 205.0 mg ± 10% | 201.5 mg | 199.6 mg | 201.6 mg | 198.7 mg | 201.3 mg |
| Dissolution test | ≧70% in 45 minutes | complies | not performed | not performed | | not performed |

-continued

T4 Soft gel matrices - Batch N° 147/IB-79, dosage: 75 μg; manufactured
March 2003 - start stability March 2003 - contained in blister ACCLAR

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Microbial controls: | Aerobic bacteria: ≦1000 CFU/g Moulds and yeasts: <100 CFU/g *Escherichia Coli*: absent/g | complies: 10 CFU/g <5 CFU/g absent/g | not performed | not performed | | not performed |

\* of the theoretical value

T4 Soft gel matrices - Batch N° 148/IB-79, dosage: 75 μg; manufactured
March 2003 - start stability March 2003 - contained in glass flacon

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.3% | 0.4% \* | 0.4% \* | <LOD (LOD = 0.9%) | <LOD (LOD = 0.9%) |
| Average assay | 90-110% of the theoretical value | 96.5% | 92.5% \* | 96.5% \* | 92.1% \* | 92.8% \* |
| Average weight | 205.0 mg ± 10% | 201.0 mg | 200.5 mg | 200.8 mg | 198.8 mg | 199.4 mg |
| Dissolution test | ≧70% in 45 minutes | complies | not performed | not performed | | not performed |
| Microbial controls: | Aerobic bacteria: ≦1000 CFU/g Moulds and yeasts: <100 CFU/g *Escherichia Coli*: absent/g | complies: 10 CFU/g <5 CFU/g absent/g | not performed | not performed | | not performed |

\* of the theoretical value

T4 Soft gel matrices - Batch N° 148/IB-79, dosage: 75 μg; manufactured
March 2003 - start stability March 2003 - contained in blister ACCLAR

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.3% | 0.4% \* | 0.4% \* | <LOD (LOD = 0.9%) | <LOD (LOD = 0.9%) |
| Average assay | 90-110% of the theoretical value | 96.5% | 91.7% \* | 95.2% \* | 91.4% \* | 92.7% \* |
| Average weight | 205.0 mg ± 10% | 201.0 mg | 200.8 mg | 200.5 mg | 198.9 mg | 199.3 mg |
| Dissolution test | ≧70% in 45 minutes | complies | not performed | not performed | | not performed |
| Microbial controls: | Aerobic bacteria: ≦1000 CFU/g Moulds and yeasts: <100 CFU/g *Escherichia Coli*: absent/g | complies: 10 CFU/g <5 CFU/g absent/g | not performed | not performed | | not performed |

T4 Soft gel matrices - Batch N° 136/IB-79, dosage: 100 μg; manufactured February 2003 - start stability March 2003 - contained in glass flacon

| Test | Stability specifications | T0 | 3 months 30° C. ± 2° C./ 60% ± 5% R.H. | 3 months 25° C. ± 2° C./ 60% ± 5% R.H. | 6 months 30° C. ± 2° C./ 60% ± 5% R.H. | 6 months 25° C. ± 2° C./ 60% ± 5% R.H. |
|---|---|---|---|---|---|---|
| Characters | round biconvex matrices, amber-coloured | complies | complies | complies | complies | complies |
| Degradation product ($T_3$ content) | ≦4% | 0.2% | 0.3% * | 0.3% * | <LOD (LOD = 0.7%) | <LOD (LOD = 0.7%) |
| Average assay | 90-110% of the theoretical value | 97.6% | 96.1% * | 96.5% * | 94.0% * | 94.6% * |
| Average weight | 205.0 mg ± 10% | 205.3 mg | 204.5 mg | 203.5 mg | 202.4 mg | 201.9 mg |
| Dissolution test | ≧70% in 45 minutes | complies | not performed | not performed | not performed | not performed |
| Microbial controls: | Aerobic bacteria: ≦1000 CFU/g Moulds and yeasts: <100 CFU/g *Escherichia Coli*: absent/g | complies: <5 CFU/g absent/g | <5 CFU/g not performed | not performed | not performed | not performed |

* of the theoretical value

T4 Soft gel matrices - Batch N° 136/IB-79, dosage: 100 μg; manufactured February 2003 - start stability March 2003 - contained in blister ACCLAR

| Test | Stability specifications | T0 | 3 months 30° C. ± 2° C./ 60% ± 5% R.H. | 3 months 25° C. ± 2° C./ 60% ± 5% R.H. | 6 months 30° C. ± 2° C./ 60% ± 5% R.H. | 6 months 25° C. ± 2° C./ 60% ± 5% R.H. |
|---|---|---|---|---|---|---|
| Characters | round biconvex matrices, amber-coloured | complies | complies | complies | complies | complies |
| Degradation product ($T_3$ content) | ≦4% | 0.2% | 0.4% * | 0.3% * | <LOD (LOD = 0.7%) | <LOD (LOD = 0.7%) |
| Average assay | 90-110% of the theoretical value | 97.6% | 94.9% * | 97.0% * | 93.1% * | 97.0% * |
| Average weight | 205.0 mg ± 10% | 205.3 mg | 203.0 mg | 203.2 mg | 203.9 mg | 206.9 mg |
| Dissolution test | ≧70% in 45 minutes | complies | not performed | not performed | not performed | not performed |
| Microbial controls: | Aerobic bacteria: ≦1000 CFU/g Moulds and yeasts: <100 CFU/g *Escherichia Coli*: absent/g | complies: <5 CFU/g absent/g | <5 CFU/g not performed | not performed | not performed | not performed |

* of the theoretical value

T4 Soft gel matrices - Batch N° 149/IB-79, dosage: 125 μg; manufactured March 2003 - start stability March 2003 - contained in glass flacon

| Test | Stability specifications | T0 | 3 months 30° C. ± 2° C./ 60% ± 5% R.H. | 3 months 25° C. ± 2° C./ 60% ± 5% R.H. | 6 months 30° C. ± 2° C./ 60% ± 5% R.H. | 6 months 25° C. ± 2° C./ 60% ± 5% R.H. |
|---|---|---|---|---|---|---|
| Characters | round biconvex matrices, amber-coloured | complies | complies | complies | complies | complies |
| Degradation product ($T_3$ content) | ≦4% | 0.1% | 0.3% * | 0.2% * | <LOD (LOD = 0.6%) | <LOD (LOD = 0.6%) |

-continued

T4 Soft gel matrices - Batch N° 149/IB-79, dosage: 125 μg; manufactured March 2003 - start stability March 2003 - contained in glass flacon

| | | | 3 months | | 6 months | |
| --- | --- | --- | --- | --- | --- | --- |
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Average assay | 90-110% of the theoretical value | 97.3% | 99.6% * | 99.5% * | 97.6% * | 97.8% * |
| Average weight | 205.0 mg ± 10% | 198.7 mg | 200.4 mg | 199.5 mg | 198.6 mg | 197.9 mg |
| Dissolution test | ≧70% in 45 minutes | complies | not performed | not performed | not performed | not performed |
| Microbial controls: | Aerobic bacteria: ≦1000 CFU/g Moulds and yeasts: <100 CFU/g *Escherichia Coli*: absent/g | complies: 5 CFU/g <5 CFU/g absent/g | not performed | not performed | not performed | not performed |

* of the theoretical value

T4 Soft gel matrices - Batch N° 149/IB-79, dosage: 125 μg; manufactured March 2003 - start stability March 2003 - contained in blister ACCLAR

| | | | 3 months | | 6 months | |
| --- | --- | --- | --- | --- | --- | --- |
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.1% | 0.3% * | 0.3% * | <LOD (LOD = 0.6%) | <LOD (LOD = 0.6%) |
| Average assay | 90-110% of the theoretical value | 97.3% | 99.5% * | 99.7% * | 97.1% * | 98.5% * |
| Average weight | 205.0 mg ± 10% | 198.7 mg | 200.1 mg | 199.3 mg | 200.4 mg | 198.9 mg |
| Dissolution test | ≧70% in 45 minutes | complies | not performed | not performed | not performed | not performed |
| Microbial controls: | Aerobic bacteria: ≦1000 CFU/g Moulds and yeasts: <100 CFU/g *Escherichia Coli*: absent/g | complies: 5 CFU/g <5 CFU/g absent/g | not performed | not performed | not performed | not performed |

* of the theoretical value

T4 Soft gel matrices - Batch N° 150/IB-79, dosage: 150 μg; manufactured March 2003 - start stability March 2003 - contained in glass flacon

| | | | 3 months | | 6 months | |
| --- | --- | --- | --- | --- | --- | --- |
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.1% | 0.2% * | 0.2% * | <LOD (LOD = 0.5%) | <LOD (LOD = 0.5%) |
| Average assay | 90-110% of the theoretical value | 99.2% | 94.4% * | 96.1% * | 95.7% * | 96.6% * |
| Average weight | 205.0 mg ± 10% | 200.8 mg | 201.1 mg | 201.4 mg | 199.8 mg | 198.5 mg |
| Dissolution test | ≧70% in 45 minutes | complies | not performed | not performed | not performed | not performed |

-continued

T4 Soft gel matrices - Batch N° 150/IB-79, dosage: 150 µg; manufactured
March 2003 - start stability March 2003 - contained in glass flacon

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Microbial controls: | Aerobic bacteria: ≦1000 CFU/g Moulds and yeasts: <100 CFU/g *Escherichia Coli*: absent/g | complies: 25 CFU/g <5 CFU/g absent/g | not performed | not performed | | not performed |

\* of the theoretical value

T4 Soft gel matrices - Batch N° 150/IB-79, dosage: 150 µg; manufactured
March 2003 - start stability March 2003 - contained in blister ACCLAR

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.1% | 0.3% \* | 0.2% \* | <LOD (LOD = 0.5%) | <LOD (LOD = 0.5%) |
| Average assay | 90-110% of the theoretical value | 99.2% | 94.5% \* | 97.5% \* | 94.1% \* | 96.2% \* |
| Average weight | 205.0 mg ± 10% | 200.8 mg | 199.6 mg | 201.2 mg | 200.1 mg | 198.9 mg |
| Dissolution test | ≧70% in 45 minutes | complies | not performed | not performed | | not performed |
| Microbial controls: | Aerobic bacteria: ≦1000 CFU/g Moulds and yeasts: ≦100 CFU/g *Escherichia Coli*: absent/g | complies: 25 CFU/g <5 CFU/g absent/g | not performed | not performed | | not performed |

\* of the theoretical value

T4 Soft gel matrices - Batch N° 151/IB-79, dosage: 150 µg; manufactured March 2003 - start stability March 2003 - contained in glass flacon

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.1% | 0.2% \* | 0.2% \* | <LOD (LOD = 0.5%) | <LOD (LOD = 0.5%) |
| Average assay | 90-110% of the theoretical value | 97.2% | 94.3% \* | 97.7% \* | 95.5% \* | 96.9% \* |
| Average weight | 205.0 mg ± 10% | 200.4 mg | 201.7 mg | 201.7 mg | 198.1 mg | 198.7 mg |
| Dissolution test | ≧70% in 45 minutes | complies | not performed | not performed | | not performed |
| Microbial controls: | Aerobic bacteria: ≦1000 CFU/g Moulds and yeasts: ≦100 CFU/g *Escherichia Coli*: absent/g | complies: 30 CFU/g <5 CFU/g absent/g | not performed | not performed | | not performed |

\* of the theoretical value

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |

T4 Soft gel matrices - Batch N° 151/IB-79, dosage; 150 μg; manufactured March 2003 - start stability March 2003 - contained in blister ACCLAR

| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
|---|---|---|---|---|---|---|
| Characters | round biconvex matrices, amber-coloured | complies | complies | complies | complies | complies |
| Degradation product ($T_3$ content) | ≦4% | 0.1% | 0.2% * | 0.2% * | <LOD (LOD = 0.5%) | <LOD (LOD = 0.5%) |
| Average assay | 90-110% of the theoretical value | 97.2% | 95.0% * | 97.9% * | 92.9% * | 95.2% * |
| Average weight | 205.0 mg ± 10% | 200.4 mg | 200.3 mg | 202.4 mg | 200.2 mg | 200.9 mg |
| Dissolution test | ≧70% in 45 minutes | complies | not performed | not performed | not performed | not performed |
| Microbial controls: | Aerobic bacteria: ≦1000 CFU/g Moulds and yeasts: ≦100 CFU/g *Escherichia Coli*: absent/g | complies: 30 CFU/g <5 CFU/g absent/g | not performed | not performed | not performed | not performed |

* of the theoretical value

T4 Soft gel matrices - Batch N° 152/IB-79, dosage: 150 μg; manufactured March 2003 - start stability March 2003 - contained in glass flacon

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.2% | 0.2% * | 0.2% * | <LOD (LOD = 0.5%) | <LOD (LOD = 0.5%) |
| Average assay | 90-110% of the theoretical value | 96.3% | 96.2% * | 96.5% * | 95.9% * | 96.7% * |
| Average weight | 205.0 mg ± 10% | 200.0 mg | 201.7 mg | 202.7 mg | 198.5 mg | 197.3 mg |
| Dissolution test | ≧70% in 45 minutes | complies | not performed | not performed | not performed | not performed |
| Microbial controls: | Aerobic bacteria: ≦1000 CFU/g Moulds and yeasts: ≦100 CFU/g *Escherichia Coli*: absent/g | complies: 10 CFU/g <5 CFU/g absent/g | not performed | not performed | not performed | not performed |

* of the theoretical value

T4 Soft gel matrices - Batch N° 152/IB-79, dosage: 150 μg; manufactured March 2003 - start stability March 2003 - contained in blister ACCLAR

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Characters | round biconvex matrices, amber-coloured | complies | complies | complies | complies | complies |
| Degradation product ($T_3$ content) | ≦4% | 0.2% | 0.2% * | 0.2% * | <LOD (LOD = 0.5%) | <LOD (LOD = 0.5%) |

-continued

T4 Soft gel matrices - Batch N° 152/IB-79, dosage: 150 µg; manufactured March 2003 - start stability March 2003 - contained in blister ACCLAR

| | | | 3 months | | 6 months | |
|---|---|---|---|---|---|---|
| Test | Stability specifications | T0 | 30° C. ± 2° C./ 60% ± 5% R.H. | 25° C. ± 2° C./ 60% ± 5% R.H. | 30° C. ± 2° C./ 60% ± 5% R.H. | 25° C. ± 2° C./ 60% ± 5% R.H. |
| Average assay | 90-110% of the theoretical value | 96.3% | 96.0% * | 97.0% * | 95.8% * | 96.3% * |
| Average weight | 205.0 mg ± 10% | 200.0 mg | 202.5 mg | 202.5 mg | 198.6 mg | 199.2 mg |
| Dissolution test | ≧70% in 45 minutes | complies | not performed | not performed | not performed | not performed |
| Microbial controls: | Aerobic bacteria: ≦1000 CFU/g Moulds and yeasts: ≦100 CFU/g *Escherichia Coli*: absent/g | complies: 10 CFU/g <5 CFU/g absent/g | not performed | not performed | not performed | not performed |

* of the theoretical value

The invention claimed is:

1. A pharmaceutical composition in the form of a single phase uniform matrix of soft-gel for oral administration comprising thyroid hormones as active principle selected from the group consisting of T3, T4, their sodium salts and mixtures thereof in a concentration of 0.001 to 1% by weight, the single phase uniform matrix of soft-gel comprising in the dried state 30%-68% by weight of gelatine of bovine, pig or fish origin, 31-60% by weight of glycerol and 1-10% by weight of water.

2. Pharmaceutical composition according to claim 1, characterised in that it comprises, in the dried state, 32-55% by weight of glycerol and 1-10% by weight of water.

3. Pharmaceutical composition according to claim 2, characterised in that it comprises, in the dried state, 32.5-50% by weight of glycerol and 1-10% by weight of water.

4. Pharmaceutical composition according to claim 1, wherein the gelatine has a pH between 3 and 10.

5. Pharmaceutical composition according to claim 2, wherein the gelatine has a pH between 3 and 10.

6. Pharmaceutical composition according to claim 3, wherein the gelatine has a pH between 3 and 10.

7. Pharmaceutical composition according to claim 1, characterised in that it comprises 0.5-5% by weight of ethanol.

8. Pharmaceutical composition according to claim 1, characterised in that it comprises, in the dried state, 3-10% by weight of polyhydroxy or polyether alcohols, selected from the group consisting of sorbitol/sorbitans, 1,2-propyleneglycol, polyethyleneglycols, mannitol, and mixtures thereof.

9. Pharmaceutical composition according to claim 2, characterised in that it comprises, in the dried state, 3-10% by weight of polyhydroxy or polyether alcohols, selected from the group consisting of sorbitans, 1,2-propyleneglycol, polyethyleneglycols, mannitol, and mixtures thereof.

10. Pharmaceutical composition according to claim 3, characterised in that it comprises, in the dried state, 3-10% by weight of polyhydroxy or polyether alcohols, selected from the group consisting of sorbitol/sorbitans, 1,2-propyleneglycol, polyethyleneglycols, mannitol, and mixtures thereof.

11. Pharmaceutical composition according to claim 5, characterised in that it comprises, in the dried state, 3-10% by weight of polyhydroxy or polyether alcohols, selected from the group consisting of sorbitol/sorbitans, 1,2-propyleneglycol, polyethyleneglycols, mannitol, and mixtures thereof.

12. Pharmaceutical composition according to claim 1, further comprising one or more members selected from the group consisting of excipients, solid additives that modify the characteristics of the release of thyroid hormones from the uniform matrix of soft-gel, preservatives and colouring agents.

13. Pharmaceutical composition according to claim 2, further comprising one or more members selected from the group consisting of excipients, solid additives that modify the characteristics of the release of thyroid hormones from the uniform matrix of soft-gel, preservatives and colouring agents.

14. Pharmaceutical composition according to claim 3, further comprising one or more members selected from the group consisting of excipients, solid additives that modify the characteristics of the release of thyroid hormones from the uniform matrix of soft-gel, preservatives and colouring agents.

15. Pharmaceutical composition according to claim 5, further comprising one or more members selected from the group consisting of solid additives that modify the characteristics of the release of thyroid hormones from the uniform matrix of soft-gel, preservatives and colouring agents.

16. A pharmaceutical composition in the form of a single phase uniform matrix of a soft-gel for oral administration comprising a thyroid hormone, selected from the group consisting of T3, T4, their sodium salts, and mixtures thereof, as active principle in a concentration of 0.001-1% by weight, the single phase uniform matrix of soft-gel comprising, in the dried state, 30%-70% by weight of gelatine of bovine, pig or fish origin, 20-60% by weight of sorbitol/sorbitans, and 1-10% by weight of water.

17. Pharmaceutical composition according to claim 16, characterised in that it comprises, in the dried state, 25-55% by weight of sorbitol/sorbitans and 1-10% by weight of water.

18. Pharmaceutical composition according to claim 17, characterised in that it comprises, in the dried state, 25%-50% by weight of sorbitol/sorbitans and 1-10% by weight of water.

19. Pharmaceutical composition according to claim 16, wherein the gelatine has a pH between 3 and 10.

20. Pharmaceutical composition according to claim 17, wherein the gelatine has a pH between 3 and 10.

21. Pharmaceutical composition according to claim 18, wherein the gelatine has a pH between 3 and 10.

22. Pharmaceutical composition according to claim 16, characterised in that it comprises 0.5-5% in weight of ethanol.

23. Pharmaceutical composition according to claim 17, characterised in that it comprises 0.5-5% in weight of ethanol.

24. Pharmaceutical composition according to claim 18, characterised in that it comprises 0.5-5% in weight of ethanol.

25. Pharmaceutical composition according to claim 16, characterised in that it comprises, in the dried state, 1-10% by weight of polyhydroxy or polyether alcohols, selected from the group consisting of glycerol, 1,2-propyleneglycol, polyethyleneglycols, mannitol, and mixtures thereof.

26. Pharmaceutical composition according to claim 17, characterised in that it comprises, in the dried state, 1-10% by weight of polyhydroxy or polyether alcohols, selected from the group consisting of glycerol, 1,2-propyleneglycol, polyethyleneglycols, mannitol, and mixtures thereof.

27. Pharmaceutical composition according to claim 18, characterised in that it comprises, in the dried state, 1-10% by weight of polyhydroxy or polyether alcohols, selected from the group consisting of glycerol, 1,2-propyleneglycol, polyethyleneglycols, mannitol, and mixtures thereof.

28. Pharmaceutical composition according to claim 22, characterised in that it comprises, in the dried state, 1-10% by weight of polyhydroxy or polyether alcohols, selected from the group consisting of glycerol, 1,2-propyleneglycol, polyethyleneglycols, mannitol, and or mixtures thereof 29. Pharmaceutical composition according to claim 16, further comprising one or more members selected from the group consisting of solid additives that modify the characteristics of the release of thyroid hormones from the uniform matrix of soft-gel, preservatives and colouring agents.

30. Pharmaceutical composition according to claim 17, further comprising one or more members selected from the group consisting of solid additives that modify the characteristics of the release of thyroid hormones from the uniform matrix of soft-gel, preservatives and colouring agents.

31. Pharmaceutical composition according to claim 18, further comprising one or more members selected from the group consisting of solid additives that modify the characteristics of the release of thyroid hormones from the uniform matrix of soft-gel, preservatives and colouring agents.

32. Pharmaceutical composition according to claim 22, further comprising one or more members selected from the group consisting of solid additives that modify the characteristics of the release of thyroid hormones from the uniform matrix of soft-gel, preservatives and colouring agents.

* * * * *